(12) United States Patent
Fish

(10) Patent No.: US 7,435,384 B2
(45) Date of Patent: Oct. 14, 2008

(54) DIAGNOSTIC INSTRUMENT WITH MOVABLE ELECTRODE MOUNTING MEMBER AND METHODS FOR DETECTING ANALYTES

(76) Inventor: Leonard Fish, P.O. Box 7891, Newport Beach, CA (US) 92658

( * ) Notice: Subject to any disclaimer, the term of this patent is extended or adjusted under 35 U.S.C. 154(b) by 678 days.

(21) Appl. No.: 10/250,754

(22) PCT Filed: Jan. 8, 2002

(86) PCT No.: PCT/US02/00461

§ 371 (c)(1),
(2), (4) Date: Feb. 6, 2004

(87) PCT Pub. No.: WO02/054052

PCT Pub. Date: Jul. 11, 2002

(65) Prior Publication Data

US 2004/0132220 A1    Jul. 8, 2004

(51) Int. Cl.
*G01N 27/00* (2006.01)
*G01N 33/50* (2006.01)
(52) U.S. Cl. .............. 422/82.02; 422/81; 422/82.01; 422/82.03; 436/86; 436/87; 436/94; 436/525
(58) Field of Classification Search .......... 422/81, 422/82.01–82.04; 436/86–87, 94, 151, 525–526, 436/537, 540
See application file for complete search history.

(56) References Cited

U.S. PATENT DOCUMENTS

| | | |
|---|---|---|
| 3,799,742 A | 3/1974 | Coleman |
| 4,021,117 A | 5/1977 | Gohde |
| 4,054,646 A | 10/1977 | Giaever |
| 4,072,576 A | 2/1978 | Arwin et al. |
| 4,218,298 A | 8/1980 | Shimada et al. |
| 4,219,335 A | 8/1980 | Ebersole |

(Continued)

FOREIGN PATENT DOCUMENTS

JP    9244055 A2    9/1997

(Continued)

OTHER PUBLICATIONS

Mosbach, M. et al, Sensors and Actuators B 2000, 70, 145-152.*

(Continued)

*Primary Examiner*—Arlen Soderquist
(74) *Attorney, Agent, or Firm*—John J. Connors; Connors & Assoc. Inc.

(57) ABSTRACT

An instrument (A) detects in a sample the presence of an analyte. The sample includes electrically readable particles (126) with an agent attached thereto that binds with the analyte or is an analog of the analyte. The instrument includes a port for the sample and a pair of electrodes (25, 30), one of which has a surface portion (30a) with an agent thereat that binds with the analyte or is an analog of the analyte. The electrodes have a first position where they are separated a sufficient distance apart to enable the sample to move between the electrodes and a second position where the electrodes are in close proximity. A detection circuit, including the electrodes, has a first state when the analyte is absent and a second state when the analyte is present. A signaling device provides an indication of the state of the detection circuit.

7 Claims, 30 Drawing Sheets

U.S. PATENT DOCUMENTS

| | | | |
|---|---|---|---|
| 4,225,410 A * | 9/1980 | Pace ........................... 204/412 |
| 4,233,144 A | 11/1980 | Pace et al. |
| 4,287,300 A | 9/1981 | Gibbons et al. |
| 4,313,929 A | 2/1982 | Morita |
| 4,440,638 A | 4/1984 | Judy |
| 4,444,892 A | 4/1984 | Malmros |
| 4,627,445 A * | 12/1986 | Garcia et al. ................ 600/583 |
| 4,632,901 A | 12/1986 | Valkirs et al. |
| 4,753,776 A | 6/1988 | Hillman |
| 4,822,566 A * | 4/1989 | Newman ................ 422/82.01 |
| 4,840,893 A | 6/1989 | Hill et al. |
| 4,859,306 A | 8/1989 | Siddiqi et al. |
| 4,859,421 A | 8/1989 | Apicella |
| 4,918,025 A | 4/1990 | Grenner |
| 4,920,047 A | 4/1990 | Giaever et al. |
| 4,945,045 A | 7/1990 | Forrest et al. |
| 4,963,245 A * | 10/1990 | Weetall ........................ 506/9 |
| 4,965,187 A | 10/1990 | Tonelli |
| 4,995,402 A * | 2/1991 | Smith et al. ................ 600/584 |
| 5,053,197 A | 10/1991 | Bowen |
| 5,063,081 A | 11/1991 | Cozzette et al. |
| 5,080,865 A * | 1/1992 | Leiner et al. ............... 422/68.1 |
| 5,114,674 A * | 5/1992 | Stanbro et al. ................ 422/57 |
| 5,114,859 A * | 5/1992 | Kagenow .................... 436/50 |
| 5,133,937 A | 7/1992 | Frackleton et al. |
| 5,141,868 A * | 8/1992 | Shanks et al. ............ 435/287.9 |
| 5,156,810 A | 10/1992 | Ribi |
| 5,167,922 A | 12/1992 | Long |
| 5,187,096 A * | 2/1993 | Giaever et al. ........... 435/287.1 |
| 5,198,368 A | 3/1993 | Khalil et al. |
| 5,217,905 A | 6/1993 | Marchand et al. |
| 5,223,219 A | 6/1993 | Subramanian et al. |
| 5,248,303 A | 9/1993 | Margolin |
| 5,281,539 A * | 1/1994 | Schramm ............... 204/403.11 |
| 5,284,748 A | 2/1994 | Mroczkowski et al. |
| 5,334,538 A | 8/1994 | Parker et al. |
| 5,359,038 A | 10/1994 | Padron |
| 5,399,486 A | 3/1995 | Cathey et al. |
| 5,401,378 A | 3/1995 | King et al. |
| 5,427,915 A | 6/1995 | Ribi et al. |
| 5,478,526 A * | 12/1995 | Sakai et al. .................... 422/81 |
| 5,503,985 A | 4/1996 | Cathey et al. |
| 5,532,128 A * | 7/1996 | Eggers et al. ................ 435/6 |
| 5,542,915 A | 8/1996 | Edwards et al. |
| 5,554,339 A | 9/1996 | Cozzette et al. |
| 5,569,406 A | 10/1996 | Barnhorst |
| 5,580,794 A | 12/1996 | Allen |
| 5,607,646 A * | 3/1997 | Okano et al. ................ 422/101 |
| 5,616,467 A | 4/1997 | Olsen et al. |
| 5,653,939 A * | 8/1997 | Hollis et al. .................. 506/3 |
| 5,660,993 A | 8/1997 | Cathey et al. |
| 5,698,406 A | 12/1997 | Cathey et al. |
| 5,714,390 A | 2/1998 | Hallowitz et al. |
| 5,730,940 A * | 3/1998 | Nakagawa ................ 422/68.1 |
| 5,744,358 A | 4/1998 | Jackowski |
| 5,776,713 A | 7/1998 | Garner et al. |
| 5,798,215 A | 8/1998 | Cathey et al. |
| 5,865,804 A | 2/1999 | Bachynsky |
| 5,898,005 A | 4/1999 | Singh et al. |
| 5,900,481 A | 5/1999 | Lough et al. |
| 5,955,377 A | 9/1999 | Maul et al. |
| 5,981,203 A | 11/1999 | Meyerhoff et al. |
| 6,013,170 A | 1/2000 | Meade |
| 6,013,459 A | 1/2000 | Meade |
| 6,024,883 A | 2/2000 | Jewell |
| 6,060,023 A | 5/2000 | Maracas |
| 6,103,538 A | 8/2000 | Kotsugai |
| 6,130,037 A * | 10/2000 | Lennox et al. ................ 435/6 |
| 6,133,046 A * | 10/2000 | Clerc ........................ 436/501 |
| 6,143,164 A | 11/2000 | Heller et al. |
| 6,300,141 B1 * | 10/2001 | Segal et al. ............. 435/287.1 |
| 6,333,200 B1 * | 12/2001 | Kaler et al. ................ 436/518 |
| 6,548,311 B1 * | 4/2003 | Knoll ........................ 436/524 |

FOREIGN PATENT DOCUMENTS

| | | | |
|---|---|---|---|
| JP | 10-239240 | * | 9/1998 |
| WO | 99/27367 | * | 6/1999 |

OTHER PUBLICATIONS

Wong et al, Convalently-Functionalized Single Walled Carbon Nanotube Probe Tips For Chemical Force Microscopy, May 22, 1998, 2 pages.

Goldin et al, The Great Out Of The Small, Jan. 3, 2001, 24 pages.

* cited by examiner

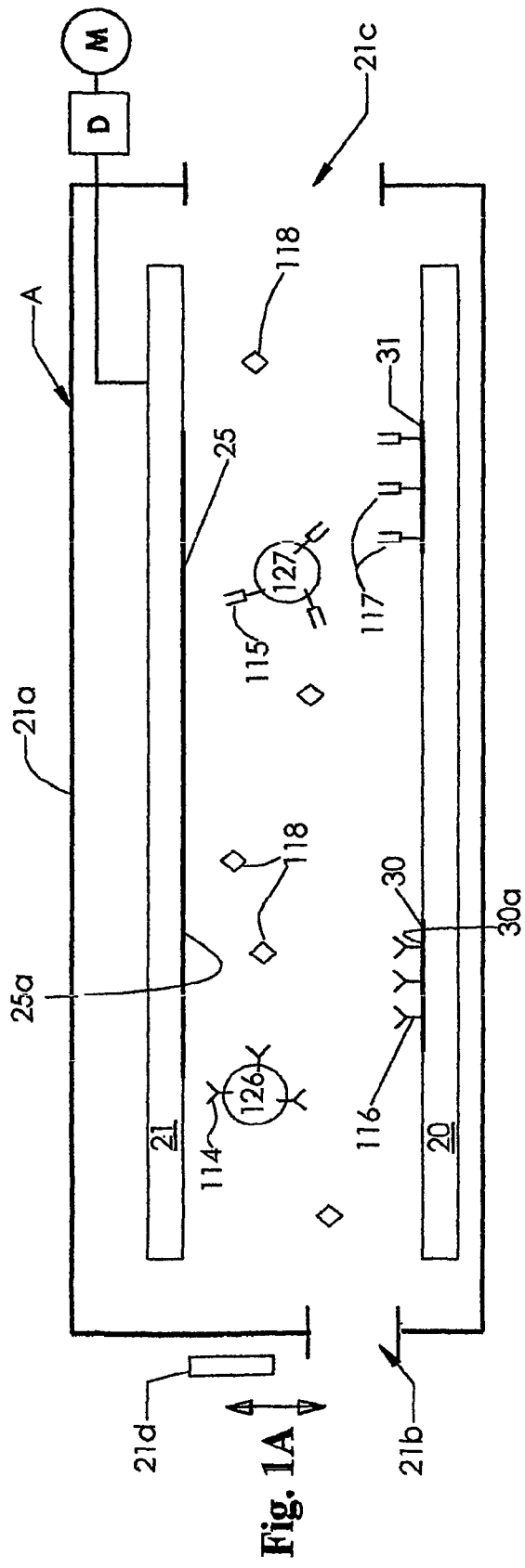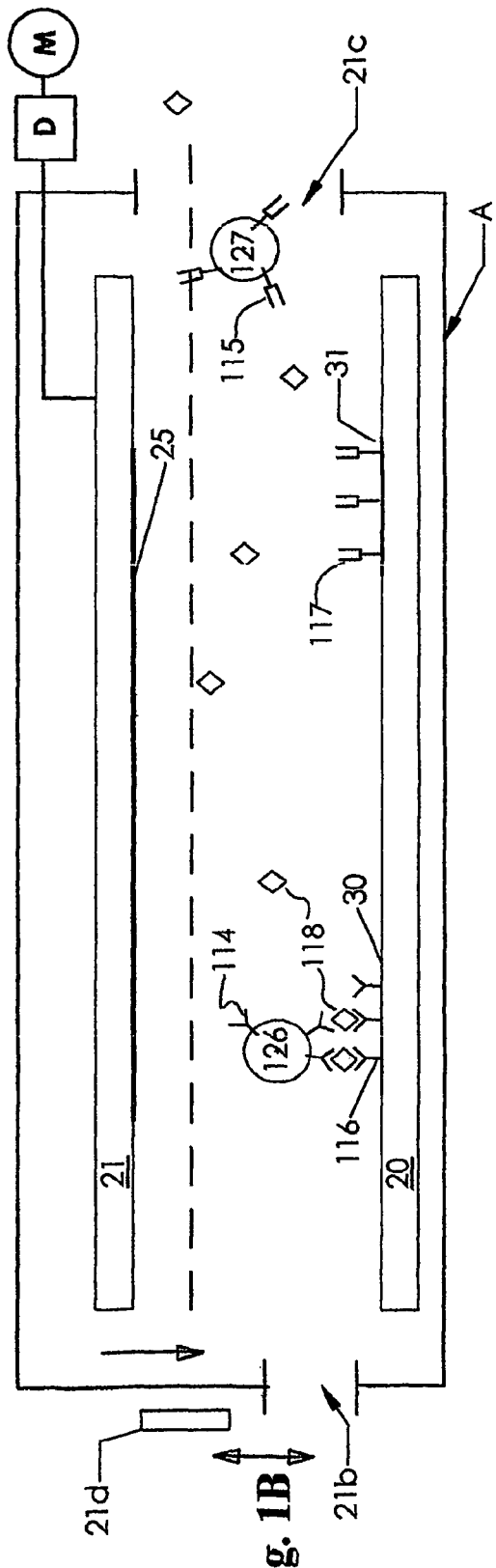

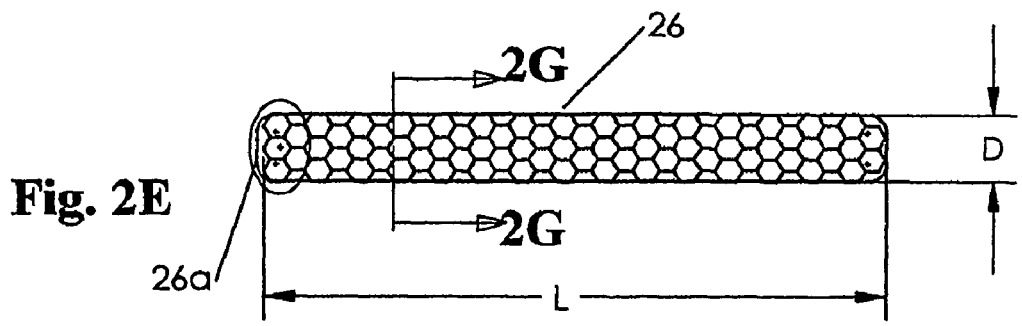
Fig. 2E
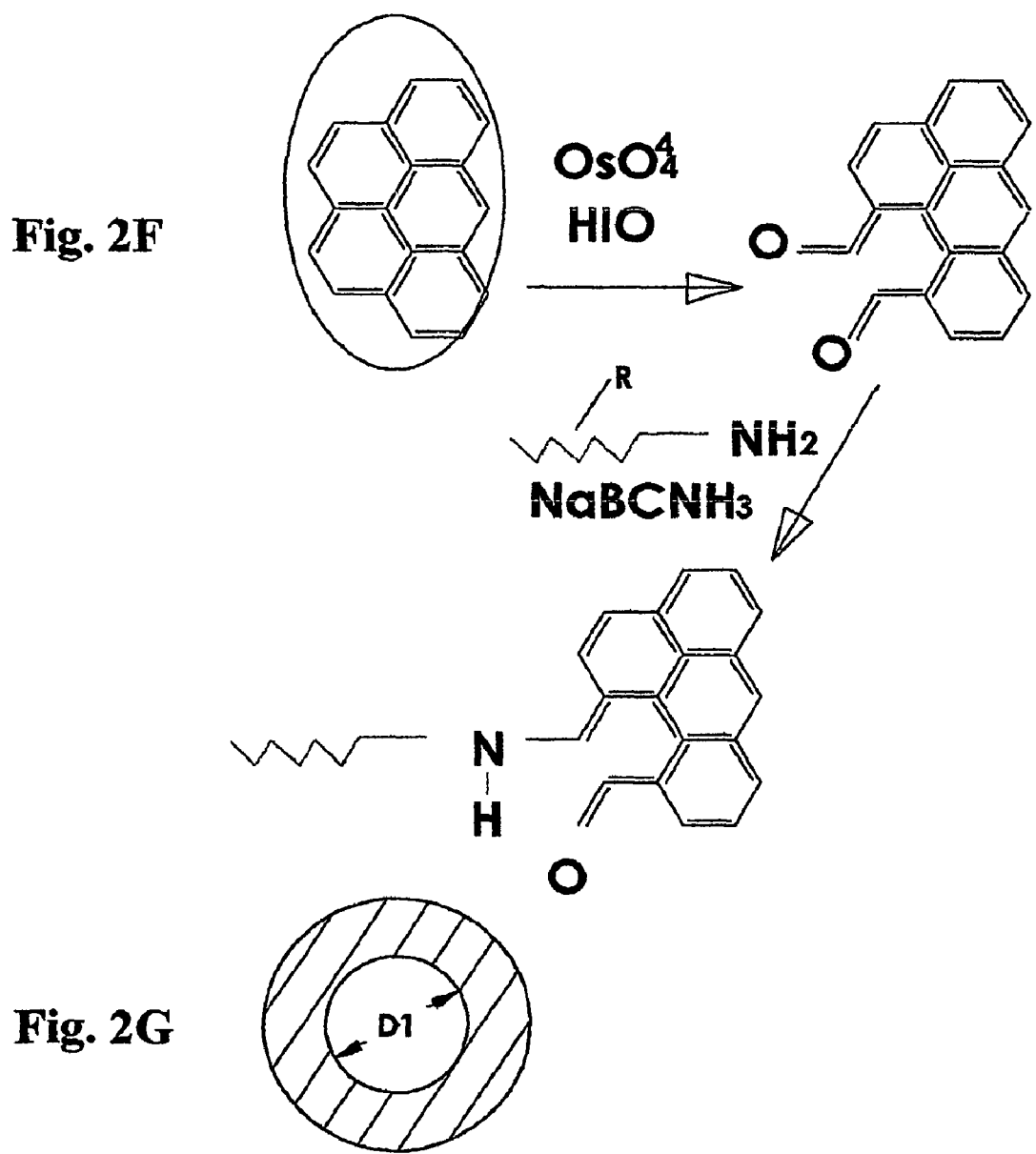
Fig. 2F
Fig. 2G

Top View

Cross Section

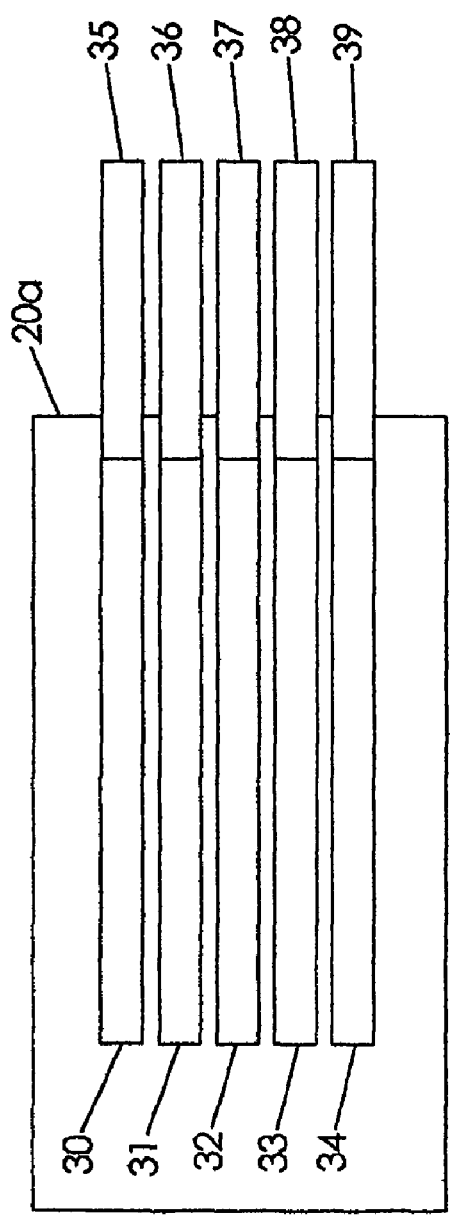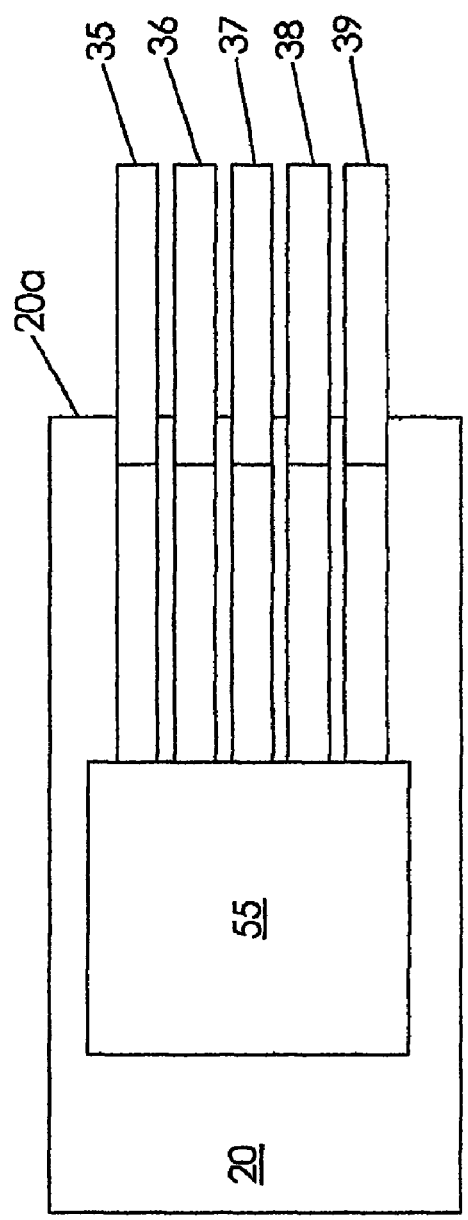
Fig. 11E
Fig. 11F

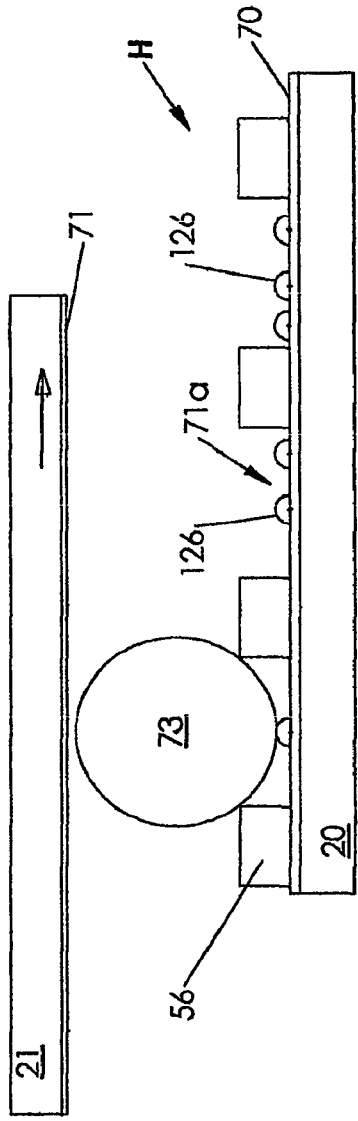
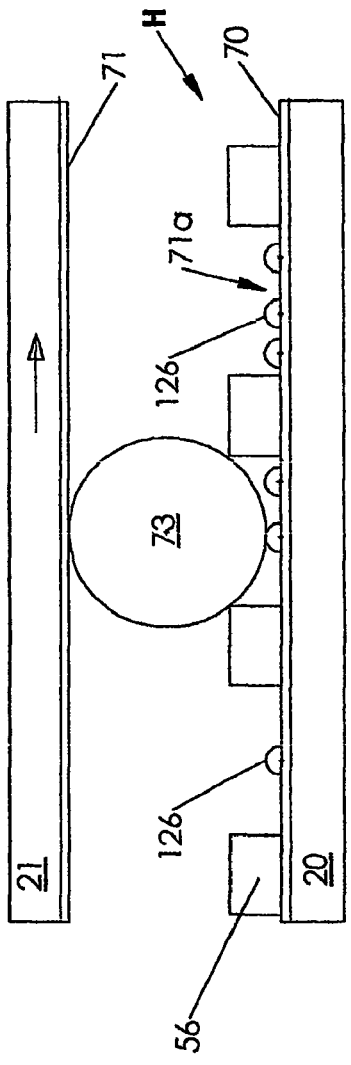
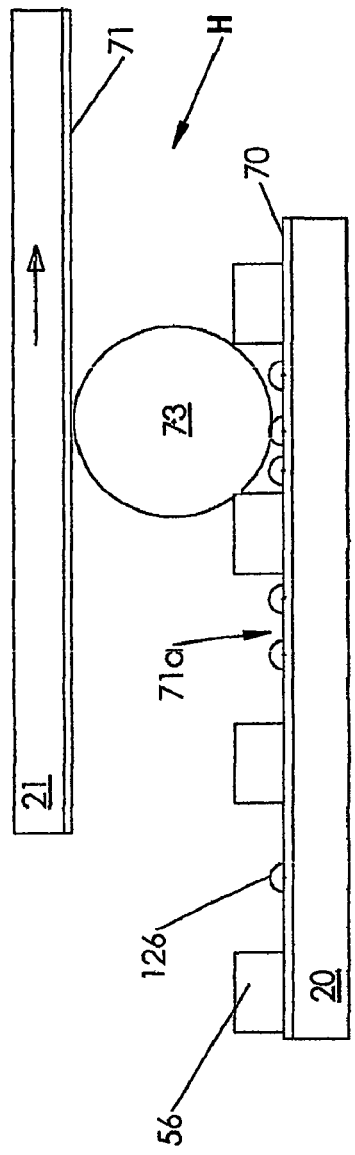
Fig. 15A
Fig. 15B
Fig. 15C

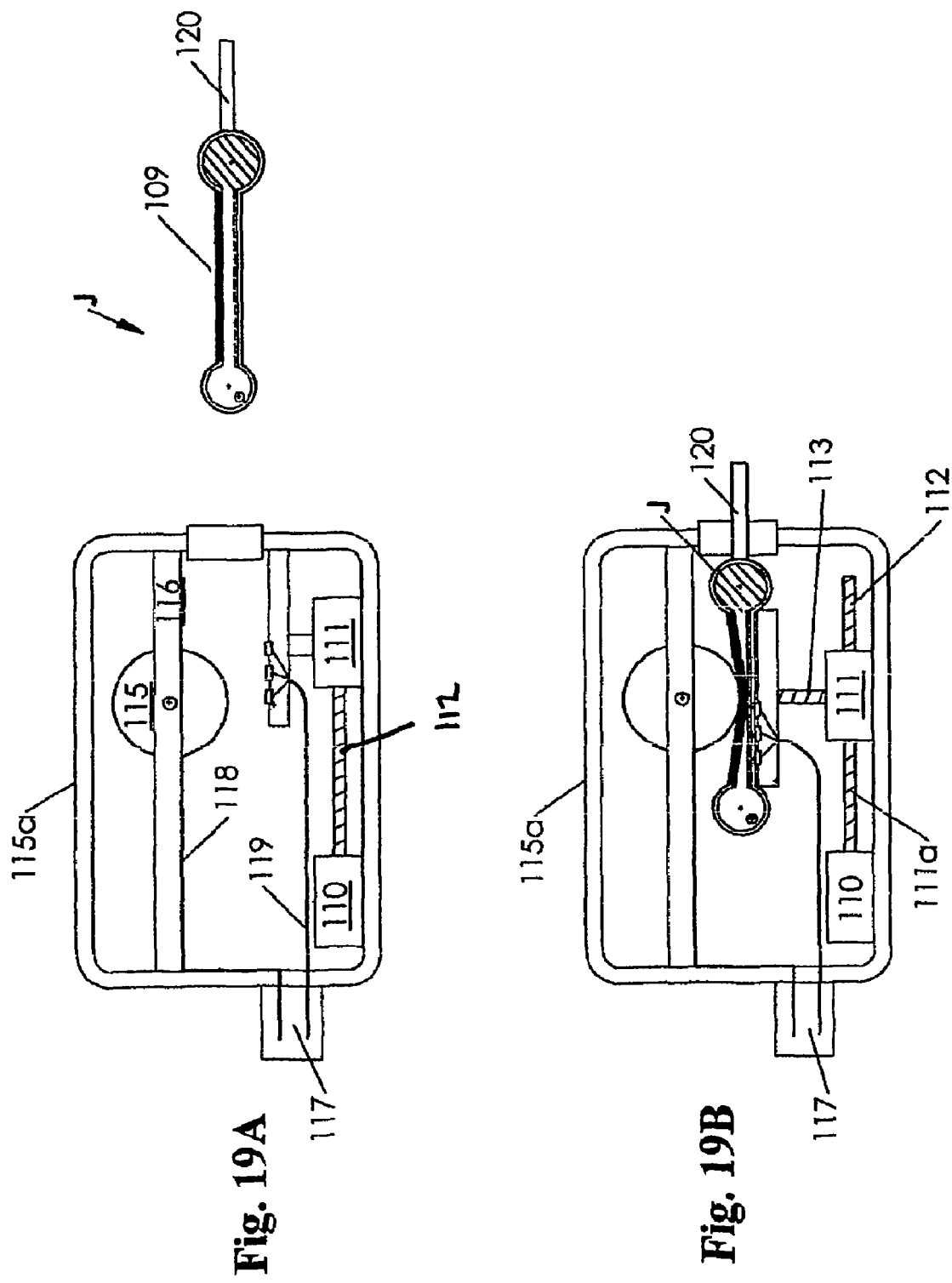

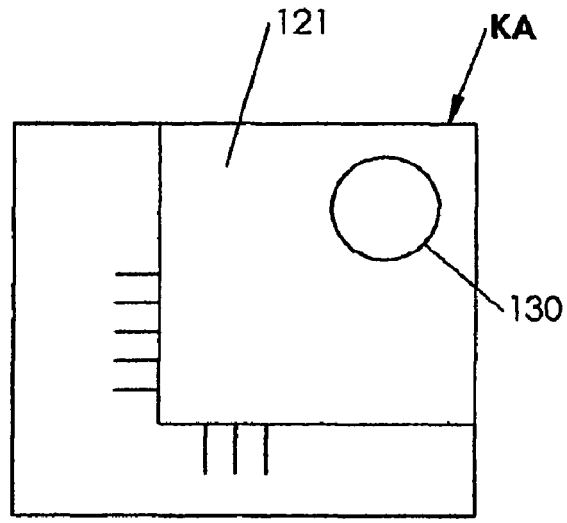
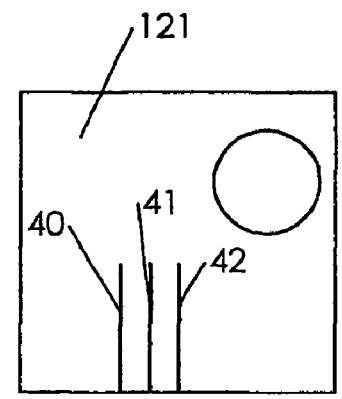
Fig. 21A   Fig. 21B
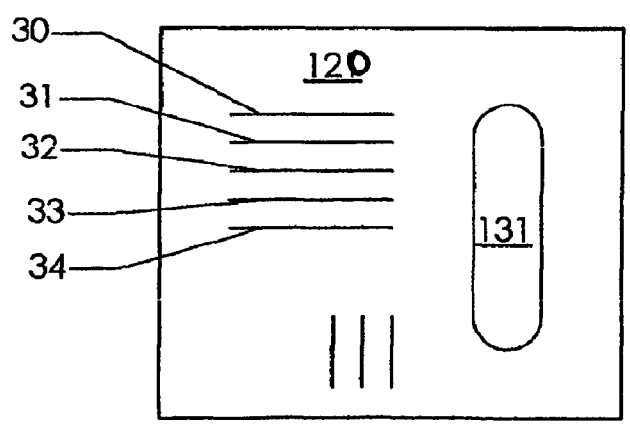
Fig. 21C

DIAGNOSTIC INSTRUMENT WITH MOVABLE ELECTRODE MOUNTING MEMBER AND METHODS FOR DETECTING ANALYTES

RELATED PATENT APPLICATIONS

This application is utility patent application based on a PCT application international application number PCT/US02/00461, international filing date Jan. 8, 2002, which in turn is based on U.S. provisional patent application Ser. No. 60/260,250, entitled "Diagnostic Instruments And Methods For Detecting Analytes," filed Jan. 8, 2001. These related applications are incorporated herein by reference and made a part of this application.

DEFINITIONS

As used herein:

"analyte" means any molecule that is in a sample and is being assayed (analyzed);

"analog of an analyte" means a chemically modified analyte, such as, for example, an analyte molecule connected to a linker molecule and will not bind with the analyte;

"binding agent" means any molecule or group of molecules that that are able to interact with an analyte;

"class of analyte" means a group of analytes that are detected b y closely similar methods: There are five main classes of clinically relevant analytes: Class I proteins, Class II nucleotides such as, for example, RNA and DNA, Class III small molecules, Class IV electrolytes, and Class V cell detection;

"electrically readable particle or particles" means a particle or particles whose physical state, or presence or absence, can be determined through the use of an electronic circuit.

"electrolyte or electrolytes" means a compound or compounds that when dissolved in an aqueous medium dissociate into ions that make the medium conductive.

"small molecule or molecules" means a molecule or molecules that do not have binding sites and have, or may be modified to have, associated therewith an electrically detectable characteristic.

BACKGROUND OF THE INVENTION

A myriad of different clinical analysis methods for detecting the presence or absence of various classes of molecules (analytes) have been developed. These analysis methods are used widely in the biological field in detecting the presence of such molecules as proteins and other biomolecules. Proteins have been mainly analyzed by immunoassays such as RIA or ELISA format, DNA by gel or capillary electrophoresis after PCR amplification, small molecules such as glucose and cholesterol, by various color reactions, either chemical or enzymatic, and electrolytes such as sodium or chloride by ion sensitive electrodes. Recently, biochip or biodisc arrays have been developed for protein and DNA analysis. Instrumentation is widely different depending on the application.

In clinical laboratories and large hospitals hundreds of samples are processed with expensive and large automated analyzers. Smaller analyzers, such as microtiter well plate readers, are used in medium or small laboratories. The fastest growing market is the point-of-care (POC) market. Glucose and HCG (pregnancy test) are examples of well established tests in which, typically, strips or dipsticks are used. Although a glucose test by necessity is quantitative, strip tests are qualitative or semi-quantitative at best with very limited dynamic range. The current technology does not allow quantitative assays in vivo, except for oxygen and possibly for glucose.

In all tests in which analyzers are used, the sample is taken first in a separate container such as a syringe or test tube or placed on a strip. Before actual assay, an aliquot of a sample or the strip is transferred into an analyzer. Transfer adds an inconvenient and potentially harmful step, because laboratory personnel can be exposed to pathogens. Although this problem has partially been solved by a cassette and applicator instrument designed for an optical disc based assay, even then a cassette must be inserted into an optical disc.

It would be highly preferable if a sampling device, the syringe or cassette, would be able to perform the actual assay immediately without any further transfer of a sample. Furthermore, it would be desirable to perform tens, or even hundreds, of different assays for various classes of analytes from the same sample. The instrument may be disposable, and of low cost.

SUMMARY OF THE INVENTION

This invention has several features. Without limiting the scope of this invention as expressed by the claims that follow, its more prominent features will now be discussed briefly. After considering this discussion, and particularly after reading the section entitled, "DETAILED DESCRIPTION OF THE PREFERRED EMBODIMENTS," one will understand how the features of this invention provide its benefits, which include, but are not limited to, quick and accurate detection of analytes, either quantitatively or qualitatively, or both, elimination of exposure of health care workers to infection, rapid analysis of samples containing multiple analytes, and provision of low cost disposable instruments or modules. In addition to application in the medical field, this invention may be used in connection with food and water safety measurements, military, and even anti-terrorist purposes.

The first feature is that the present invention solves most, if not all, of the problems associated with the prior art by a novel electronic/mechanical approach. It provides instruments and methods to detect the presence of a selected analyte in a sample including electrically readable particles having an agent attached thereto that binds with the selected analyte (Case I). In some embodiments of this invention, however, electrically readable particles need not be employed. These embodiments take advantage of a change in electrical characteristics between a pair of movable electrodes due to changes in their displacement with respect to each other (Case II). The electrodes may be formed by a photo-resist etching process or a plating process.

When electrically readable particles are used, they have binding agents at their surfaces. These binding agents bind with the analyte. They can be antibodies, oligonucleotides, or any other type of recognition molecule. The binding interaction between the analyte and the agent precedes detection of an electrical property, or a change in the electrical. Either the absence or the attendance of this electrical property, or a change in the electrical property, is sensed by a detection circuit which determines the presence or absence of the analyte. The electrical property may be current, resistance, conductance, inductance, capacitance, voltage, magnetic flux, or a phase shift. In accordance with the present invention, an electrically readable particle is bound to an electrode by an affinity binding in order to induce a significant change in the electrical properties of the detection circuit. The effect can be much greater than is obtained by binding an electro-active moiety onto a similar electrode, even if this moiety is catalytic. Moreover, the binding of an electrically readable particle is universal and independent of the chemical nature of the binding pair.

Small molecules and electrolytes can advantageously be detected electrochemically by the present invention. Electrically readable particles are not used in assaying for small molecules and electrolytes. The embodiment of this invention that does this type of assay for either a specific small molecule or a specific electrolyte detects the absence or present of an ion current using a pair of electrodes. One electrode has a surface portion that collects thereat the specific small molecule or electrolyte, as the case may be. This one electrode is at a first polarity. The other electrode has a surface portion that collects thereat small molecules or electrolytes other than said specific small molecule or electrolyte in question. This other electrode is at a second polarity opposite said first polarity. The electrodes have (i) a first position where they are separated a sufficient distance apart to enable the sample to move there between and to suppress the ion current and (ii) a second position where the electrodes are sufficiently close to each other to establish an ion current. In the first position the electrodes are separated a first distance apart sufficient to enable the sample to move between said electrodes and a second position where the electrodes are in close proximity to each other. The first distance is, greater than the second distance.

There is a detection circuit, including the electrodes, that has a first state when the specific small molecule or electrolyte is absent from the sample and a second state when the specific small molecule electrolyte is present in the sample. A signaling device provides an indication when the detection circuit is in the second state.

Almost all clinical or chemical assays can be made using both Case I and Case II embodiments of this invention. Essentially all Class I through V molecules identified above may the assayed. The molecules include, but are not limited to, peptides, proteins, glycoproteins, oligonucleotides, DNA, RNA, steroids, lipids, lipoproteins, carbohydrates, cathecolamines, several drugs, oxygen, nitric oxide, nitrous oxide, carbon dioxide, nitro, nitroso, azo, heterocyclic compounds, isocyanates, phenols, amines, most sulfur containing compounds, such as disulphides, dithiocarbamates, thiobarbiturates, thioureas, thiols, sulphonates, sulphides, and sulphoxides, and also cations, anions, chelates, and organometallics.

In the Case I embodiments of this invention, the detection circuit measures the electrical property produced when an affinity binding occurs between the analyte and the binding agent, for example, antigen-antibody interaction, DNA hybridization, ligand-receptor binding, enzyme-substrate, or enzyme-inhibitor interaction. The detection circuit includes an electrode, and preferably, uses at least one pair of relatively large surface area electrodes that in one position are widely separated, although sub-micrometer electrodes are still within the scope of this invention. Nevertheless, an individual sub-micrometer sized particle, or group of such particles, is large enough to fill the gap between the electrodes when these electrodes are in a second position in close proximity with each other to produce a detectable change in an electrical characteristic of the detection circuit.

One Case I embodiment of the present invention has a flow through capillary with a movable wall. The capillary contains two or more electrodes, at least one of which is connected to the movable wall. At least one electrode is coated with an agent that binds to the analyte. In the presence of the analyte, electrically readable particles having a binding thereon, such as a gold spheres, are bound onto the surface of the electrode coated with a binding agent. When two electrodes are allowed to approach, so that both of them are in close proximity of the electrically readable particles, for example, a current is observed that is relative to the number of the electrically readable particles and the applied electric potential. Electrically readable particles will make the capacitor leaky. Thus, electrical properties can be changed by moving the electrodes in a controlled way into close proximity and measuring the electrical property change such as conductance, resistance, inductance, capacitance, or phase shift, in order to find out the modulation of these properties by an analyte. The instrument has a mechanism for bringing two electrodes into close proximity. The close proximity is obtained by providing an accurate moving mechanism and/or physical structures that prevent a direct contact between the electrodes and accurately space the electrodes apart a predetermined distance. This allows accurate electrochemistry to be performed quickly and at low cost.

Another Case I embodiment of the present invention comprises two opposing electrode arrays intersecting at right angles. Because the electric potential can be coupled between any pair of electrodes between two arrays, the number of high field areas, i.e., active working areas on electrodes can be much larger than the number of electrodes. A simple example is an orthogonal arrangement of two linear electrode arrays. Because two or more electrode arrays can be used, the number of tests can be quite large. The instrument in which multiple analytes are assayed simultaneously employs a microprocessor to record the electrical properties of each assay site independently, or a combination of assay sites that do not interfere with each other. This instrument is greatly simplified as compared with prior art devices employing electrode arrays and it facilitates the construction of massive, very low cost arrays.

The present invention enables, perhaps for the very first time, a disposable self-contained instrument that is able to perform hundreds, or even thousands of tests qualitatively, quantitatively, or both, and quickly from a very small amount of sample. It solves most problems associated with the prior art. The assay can be performed in the sample collection instrument. No transfer or aliquoting of the sample is required. Results are obtained fast and they are quantitative. The detection is very sensitive, because a single electrically readable particle can be detected, and only one analyte molecule is necessary for the binding of that particle. The electrode arrays may allow multiple tests to be performed from each sample. The instrument may incorporate a low cost microprocessor and display, or be inserted into an adapter for connection to a computer having a microprocessor and display.

All these advantages combined enable construction of a self-contained disposable instrument that is able to analyze quantitatively, sensitively, and quickly several different analytes simultaneously. The instrument can also be modular, so that only the sample collection and measuring unit is disposable, while processing and display units are used repeatedly, or it can be a single use, disposable hand held instrument used for specific tests, or a computer equipped with an adapter.

In a third embodiment of the instrument of this invention, disposable modules, or self-contained assay instruments for the Point-of-Care, are provided. The modules can have sample collection and processing equipment including, for example, cell separation, cell lysis, reagent storage and mixing, and analyte fractionation, such as chromatography and electrophoresis. The modules have the electrodes for actual measurement. These modules can be used in combination with a processing and display instrument that has been designed for this purpose or modules can be connected via an adapter to a computer, such as a personal computer (PC). Self-contained disposable instruments may also have processing and display capability. The information can be transferred to a permanent storage unit, such as PC hard drive, before the disposal. The measurement modules, which have a sample inlet port, are in a rack or in a conveyer belt. A pipetting robot will add samples to each module, and after a short incubation time another robot will put each module into a data collection and processing system.

This invention includes several methods. Broadly, the method of this invention detects in a sample the presence of an analyte. It includes the steps of (a) introducing into the sample electrically readable particles with an agent attached thereto that binds with the analyte or is a n analog of the analyte, (b) providing an instrument including a pair of electrodes, said electrodes having a first position where they are separated a first distance apart sufficient to enable the sample to move between said electrodes and a second position where the electrodes are in close proximity to each other, said first distance being greater than said second distance, a detection circuit, including the electrodes, that has a first state when the analyte is absent from the sample and a second state when the analyte is present in the sample, said second position determining the state of the detection circuit, a signaling device that provides an indication of the state of the detection circuit with the electrodes in the second position, (c) contacting the sample, including the electrically readable particles, with the electrodes while said electrodes are in the first position, (d) removing any unbound particles from between the electrodes, and (e) moving the electrodes to the second position.

In another method the electrically readable particles are stored on a holding electrode. These stored particles may or may not carry a binding agent. If they do not, they arrived independently at the surface of this electrode through electrostatic attraction. By reversing either the charge of the particles, or of the electrode, the non-specifically bound particles are removed, while specifically bound particles remain bound.

DESCRIPTION OF THE DRAWING

The preferred embodiments of this invention, illustrating all its features, will now be discussed in detail. These embodiments depict the novel and non-obvious instrument and methods of this invention as shown in the accompanying drawing, which is for illustrative purposes only. This drawing includes the following figures (Figs.), with like numerals indicating like parts:

FIGS. 1A and 1B are schematic illustrations of a first embodiment of the instrument of this invention depicting test sites where analytes in a sample are individual molecules with at least two spaced binding sites.

FIGS. 2C through 2G are schematic illustrations of the second embodiment of the instrument of this invention depicting using nano tubes as the conductive particles, wherein FIG. 2C shows a pair of spaced apart electrodes with nano-tubes in a sample that is between the spaced apart electrodes, FIG. 2D shows the electrodes of FIG. 2C moved into close proximity with each other and the analyte attached to the left handed assay site, FIG. 2E is a side elevational view of a nano-tube.

FIG. 2F is an illustration of an end of the nano-tube being chemically treated to form thereat a binding site, FIG. 2G is a cross-sectional view taken along line 2G-2G of FIG. 2E.

FIGS. 11A through 11G are schematic illustrations depicting the steps employed in making the grid shown in FIG. 9.

FIGS. 15A through 15C are cross-sectional views of a ninth embodiment of this invention schematically illustrating an instrument employing a roller moving past different assay sites.

FIGS. 18A through 18D show a eleventh embodiment of this invention employing a disposable module used with the portable, reusable, computer adapter shown in FIGS. 19A and 19B and is used with the computer shown in FIG. 20, wherein FIG. 18A is a cross-sectional taken along line 18A-18A of FIG. 18B, FIG. 18B is a cross-sectional taken along line 18B-18B of FIG. 18A, FIG. 18C is a cross-sectional taken along line 18C-18C of FIG. 18B, FIG. 18D is a cross-sectional taken along line 18D-18D of FIG. 18B.

FIG. 19A is a cross-section view of a computer adapter to be inserted into a USB port of the computer shown in FIG. 20, showing the disposable module of FIGS. 18A through 18D about to be inserted into the computer adapter.

FIG. 19B is a cross-section view similar to that of FIG. 19A showing the disposable module of FIGS. 18A through 18D inserted into the computer adapter.

FIGS. 21A through 21C depict schematically the twelfth embodiment of this invention showing a sample carrier to be used with the automatic testing instrument shown in FIG. 21 wherein FIG. 21A is a plan view of the sample carrier comprising the top plate shown in FIG. 21B and the bottom plate shown in FIG. 21C, FIG. 21B is a plan view of the top plate of the sample carrier, and FIG. 21C is a plan view of the bottom plate of the sample carrier.

DETAILED DESCRIPTION OF THE PREFERRED EMBODIMENTS

First Embodiment

Figure 2A:
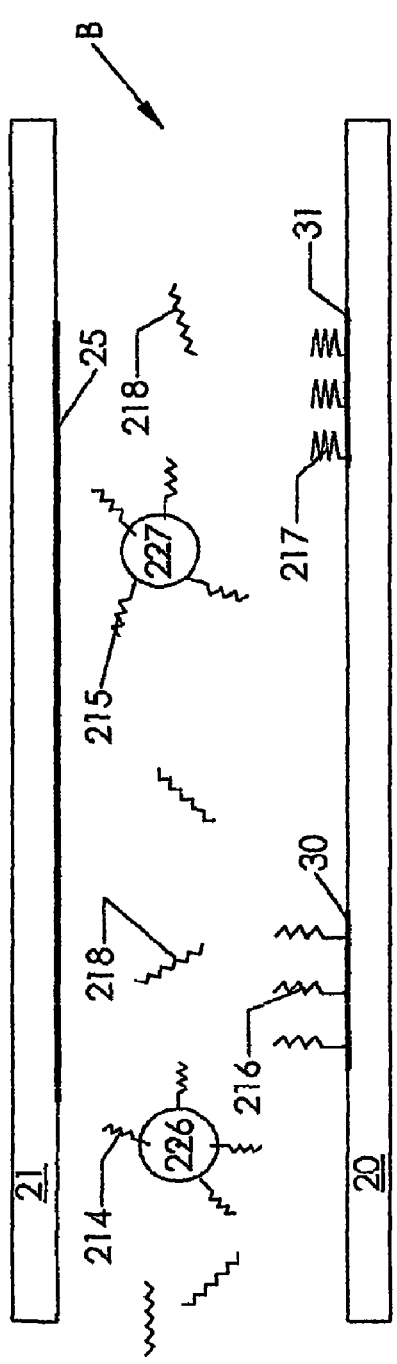
FIGS. 2A and 2B are schematic illustrations of a second embodiment of the instrument of this invention, which is similar to the first, depicting test sites where DNA specimens are the analytes in the sample.

FIG. 1 depicts an instrument A including a pair of conductive electrodes 25 and 30, respectively mounted on insulator base support members 21 and 20. The electrodes 25 and 30 have substantially flat, planar surfaces 25*a* and 30*a* facing each other and each lying in different parallel planes. These electrodes 25 and 30 are directly opposed to each other vertically, and each have an area that exceeds about 0.5 square micrometer, and typically, each have an area of from about 10 square micrometers to about 10 square millimeters. The electrodes 25 and 30 are shown in a spaced apart position in FIG. 1A and, after introducing a sample and then removing unbound material from between the electrodes 25 and 30, moved to the dotted line position shown in FIG. 1B. As shown in FIG. 1B schematically, the electrodes 25 and 30 are brought into close proximity, almost but no t quite touching. Typically, the distance between the electrodes 25 and 30, when in the position shown in FIG. 1A, is from about 5 micrometers to about 5 millimeters and, when in the position shown in FIG. 1B, is from about 10 nanometers to about 5 micrometers. A third electrode 31, spaced from the electrode 30, and also mounted on the base support 20, provides a second assay site. Binding agents 116 and 117, are respectively on the surfaces of the electrodes 30 and 31. As discussed further in connection with the embodiments shown in FIGS. 9 through 12, a plurality of pairs of directly opposed electrodes form numerous assay sites that enable an instrument according to this invention to detect several different analytes in any sample.

The base support members 21 and 20 are enclosed within a housing 21*a* having an inlet port 21*b* providing an opening in the housing through which a sample is introduced into the instrument A and an outlet port 21*c* through which sample flows from the housing. The port 21*a* may have a cover 21*d* that is moveable between open and closed positions. As illustrated, the cover 21*d* is shown in an open position. The sample includes electrically readable particles 126 and 127 and binding agents, the antibodies 114 and 115, are bound respectively to the surfaces of these electrically readable particles 126 and 127. The electrically readable particles are introduced into the sample prior to, during, or after the sample is fed into the instrument A. In this illustration, the sample also includes an analyte 118, for example, insulin. This analyte 118, having at least two spaced apart binding sites, only reacts with the binding agent 116 on the surface of the electrode 30. Upon introduction of the sample, including the particles 126 and 127 and the analyte 118, into the instrument A between the electrodes 25 and 30, the analyte attaches to the particles 126 and to the binding agent 116 on the surface of the electrode 30. Thus, on the left side, the first assay site, the electrically readable particle 126 on the electrode surface forms an antigen conductor. No affinity binding occurs on the right side, the second assay site, with the particle 127, because there are no analytes present that bind with both the binding agents 115 and 117.

Figure 12:
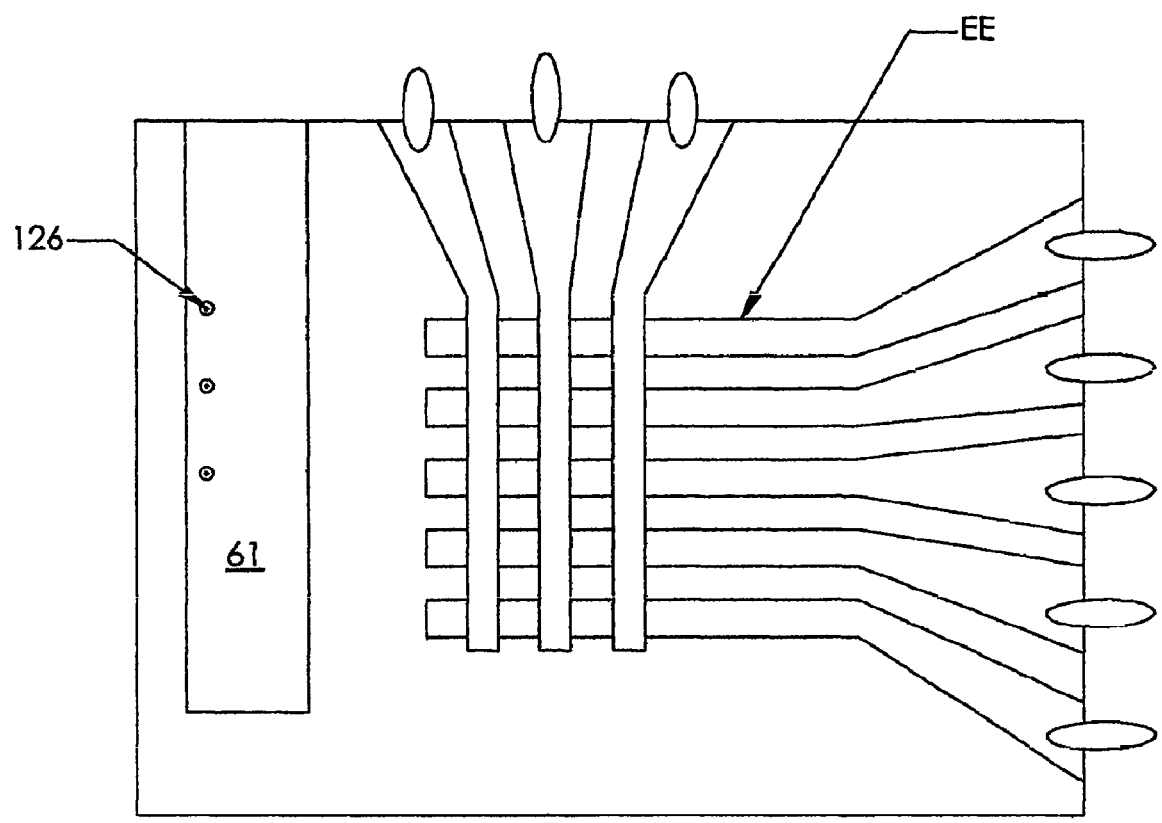
FIG. 12 is a plan view of an array of assay sites having a holding electrode in advance of the array.

In accordance with this invention, the directly opposed pairs of electrodes, electrodes 25 and 30 and electrodes 25 and 31, are moved from the position shown in FIG. 1A to the position shown in dotted line in FIG. 1B. A motor M having its output shaft (not shown) is connected to a drive mechanism D that, upon energizing the motor, moves the support member 21 downward towards the other electrodes 30 and 31 on the support 20. In the position shown in FIG. 1A, the pair of electrodes 25 and 30 is separated a sufficient distance to allow the sample to flow between this pair of electrodes and out the outlet port 21c. After an adequate time period has elapsed to allow binding to occur if the analyte 118 is present, all the assay sites are washed, for example with distilled water, to remove unbound material. An alternately mechanism such as depicted in FIG. 12 may be used. This mechanism shown in FIG. 12 will be discussed subsequently in greater detail. After washing, the motor M is energized to move the electrode to the dotted line position shown in FIG. 1B. Preferably, pressure is applied to the particle 126 bound to the electrode 30. This is especially important when the detection circuit responds to changes in conductivity. The pressure is controlled. It must not be so great as to cause a short circuit between the electrodes 25 and 30, yet sufficient to the break surface tension. The application of pressure is carefully controlled so that the electrodes pairs of an assay site do not touch, but will insure electrical contact between the particles 126 bound to the electrode 30 and also between these bound particles and the electrode 25. As discussed subsequently, a spacer device may be employed to insure that the electrodes do not touch and short out the detection circuit. When the detection circuit responds to changes in inductance, capacitance, or phase shift, the application of pressure is not critical.

Figure 23:
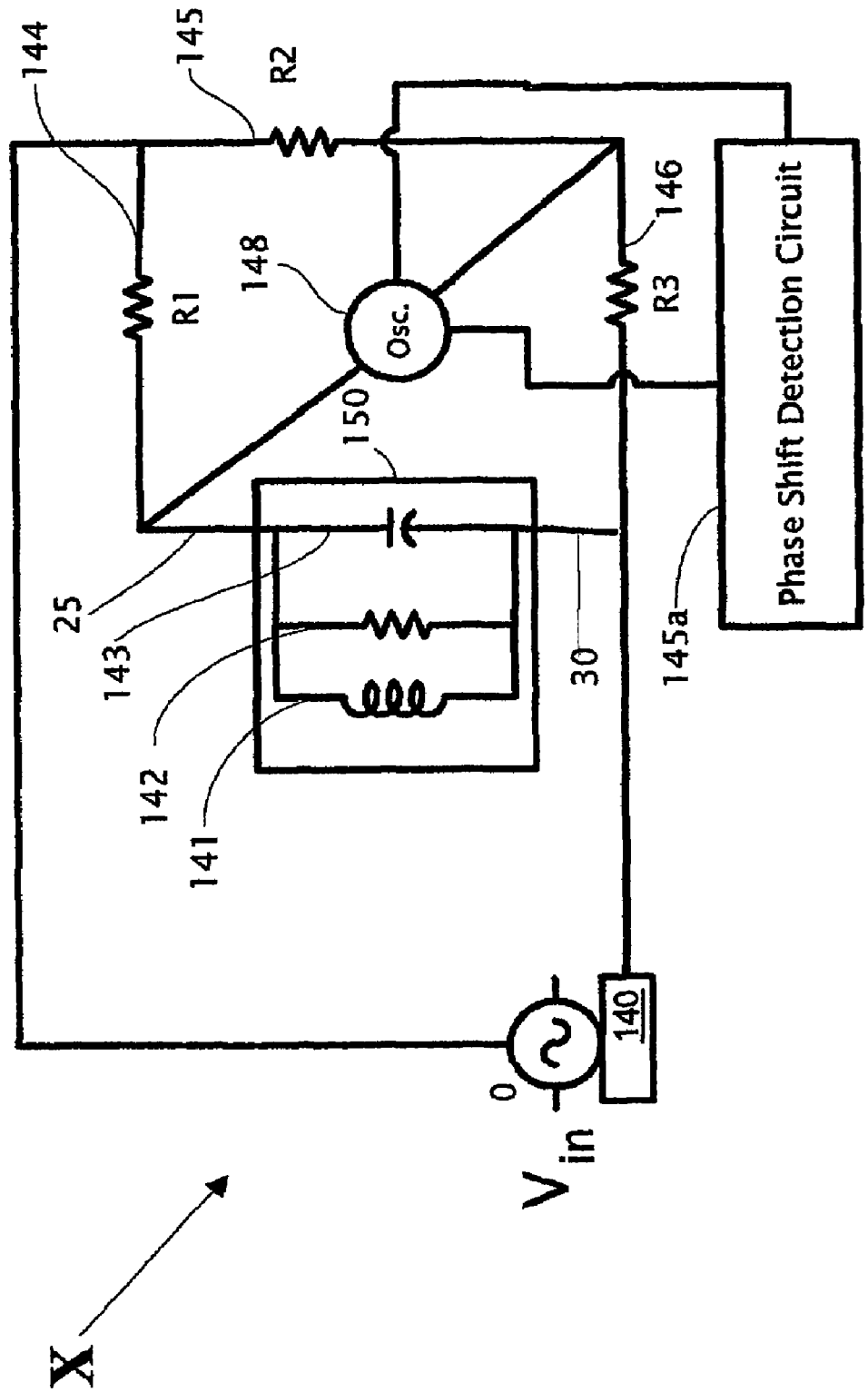
FIG. 23 is a detection circuit employed in this invention where changes in inductance, resistance and/or capacitance are detected.
Figure 24:
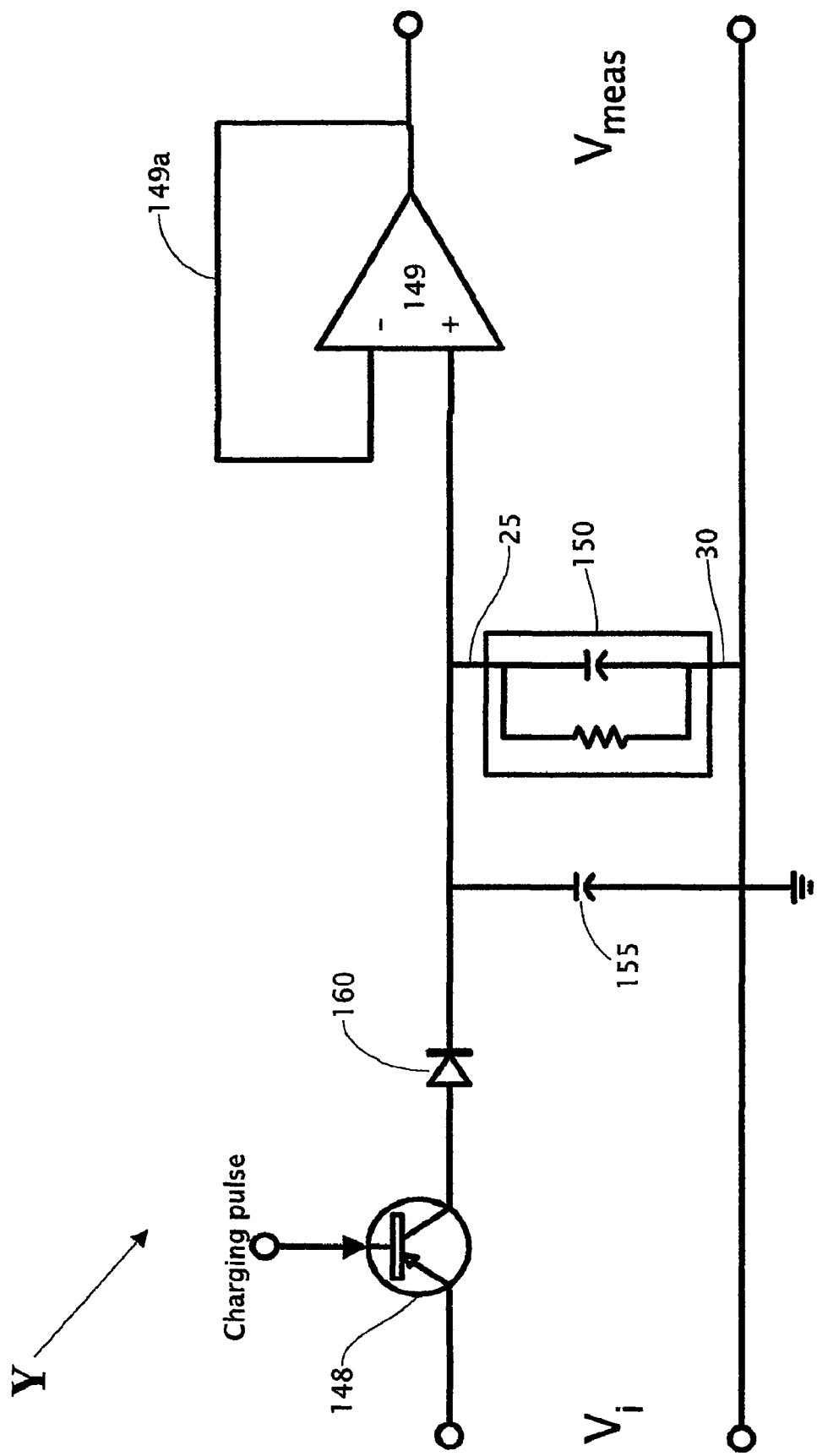
FIG. 24 is a detection circuit employed in this invention where changes in voltage are detected.
Figure 25:
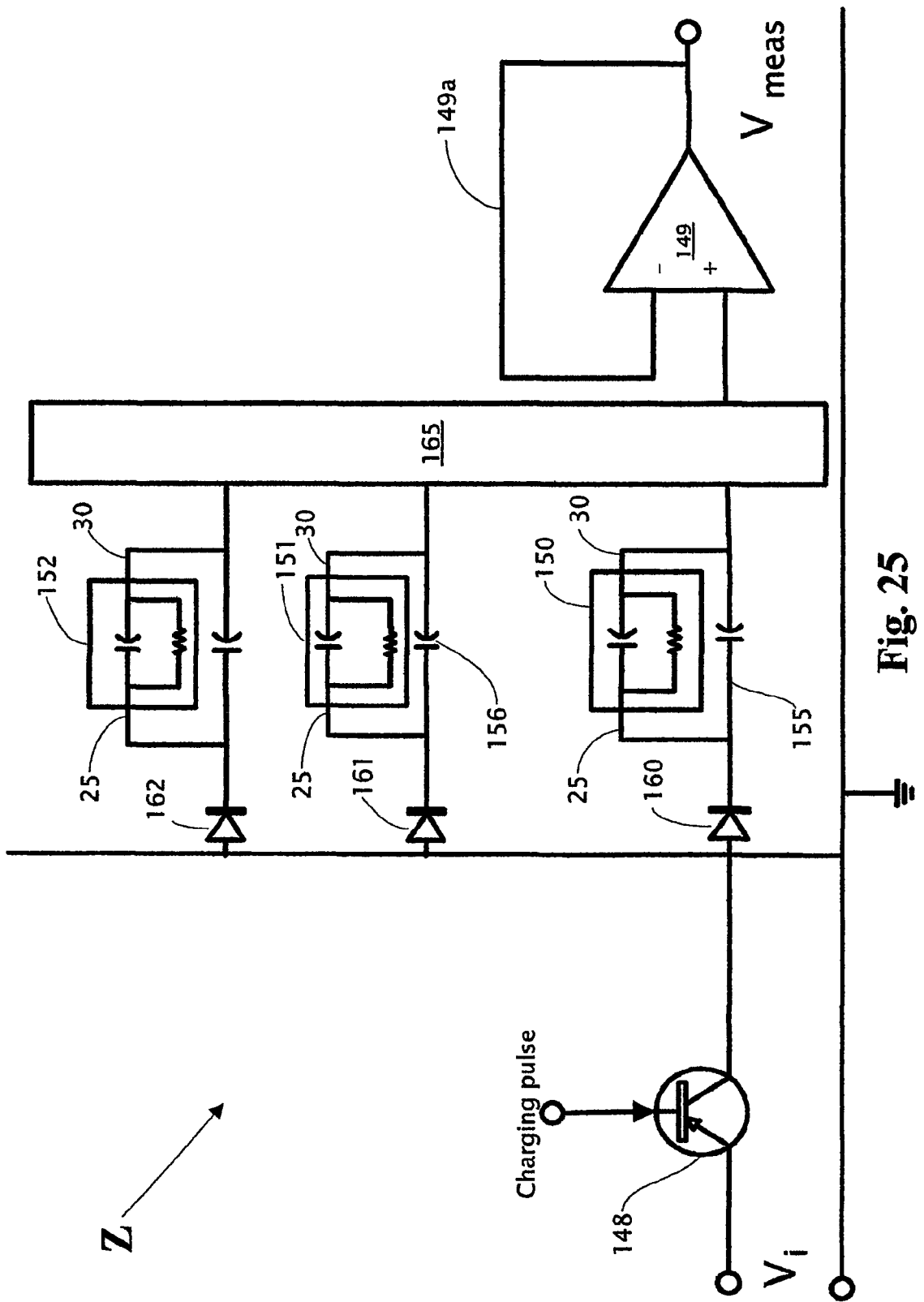
FIG. 25 is a detection circuit employed in this invention including a multiplexer.

The pairs of electrodes 25 and 30 are components in an electrical circuit such as, for example, the detection circuits depicted in FIGS. 23 through 25. These detection circuits each have a first state when the analyte is absent from the sample and a second state when the analyte is present in the sample, and a signaling device, for example, a liquid crystal display (LCD) that provides an indication when the detection circuit is in the second state. The signaling device provides a qualitative read-out identifying the analyte, or a quantitative read-out corresponding to the amount of analyte in the sample, or both. These detection circuits will be discussed in greater detail subsequently.

Because very small electrically readable particles 126 and 127 are used, the instrument A is very sensitive. It can even detect a single molecule of the analyte 118. For example, a cancer cell will produce a protein molecule or molecules that are indicative of the presence of cancer cells. In the early stages of the cancer, only very low levels of this marker protein molecule are in a sample of a subject's blood. Conventional testing techniques are not usually capable of detecting such low concentrations of these identifying protein molecules. The attachment of a single marker molecule to an electrically readable particle that is in the presence of an electrode at an assay site creates a change in state in the detection circuit that indicates the presence of this single molecule.

Second Embodiment

The second embodiment of this invention, the instrument B shown in FIG. 2, is similar to that shown in FIG. 1, but the housing 21a and motor M and drive mechanism D are not shown. This embodiment is a schematic representation of a DNA test. The electrodes 30 and 31 are coated with different probes, that is binding agents, respectively probes 216 and 217. The analyte or target 218 is able to bind with the probe 216 as well as with a probe 214 on the surface of the electrically readable particle 226. The probes 215 and 217 do not bind with the target 218. As discussed above in connection with FIGS. 1A and 1B, after binding of the target 218, unbound material is removed from the space between the electrodes 25 and 30 and the electrodes are moved towards each other and a detection circuit is then activated.

FIGS. 2C through 2G schematic represent another DNA test. In accordance with one aspect of this invention, as shown in FIGS. 2C through 2G, the conductive particles may be nano-tubes 26, such, for example, manufactured by Carbon Nanotechnologies, Inc. of Huston, Tex. Nano-tubes 26 are graphite-like elongated tubes having either opened or closed ends and hallow interiors with an outside diameter D of from about 1 nanometer to about 50 nanometers and a length L of from about 10 nanometers to about 10 micrometers. As shown in FIG. 2G, the nano-tubes 26 have an inside diameter D1 of from about 10 to 20 nanometers, with a wall thickness of an low as a single atom.

As illustrated in FIG. 2F, the opposed ends 26a and 26b of the nano-tubes have been reacted with such chemical reagents as a mixture of osium tetraoxide and periodic acid, bromine, chromic acid, or potassium permanganate, to form reactive groups. When the mixture of osium tetraoxide and periodic acid is used the reactive groups are oxygen sites. These oxygen sites are reacted with amino terminated oligonucleotides R to form at the opposed ends binding sites 26a and 26b. These binding sites on the nano-tubes 26, in the presence of the analytes 15a and 15b, which must both be present, bind with the analytes at the right hand assay site shown FIGS. 1C and 1D. There are binding agents 16 and 16a, respectively at the surfaces of the electrodes 20 and 21 that bind with the analytes attached to one nano-tubes 26. The analytes 18 do not bind with the binding agents 17 and 17a at the electrodes 21 and 20 at the right hand assay site shown in FIGS. 1C and 1D. To make the nano-tubes 26 soluble they are coated with a detergent such as tween-20. In accordance with one aspect of this invention, the electrodes 20 and 21 are more into closed proximity with each other as shown in FIG. 1D prior to measuring for attachment of the analytes to an assay site. A reference discussing chemical modification of the ends of the nano-yubes is discussed by S> S> Wong et al in Covalently-Functionalized Single-Walled Carbon Nanotube Probe Tips for Chemical Force Microscopy, J. Am. Chem. Soc. 1998, 120, 8557-8558.

Third Embodiment

Figure 3A:
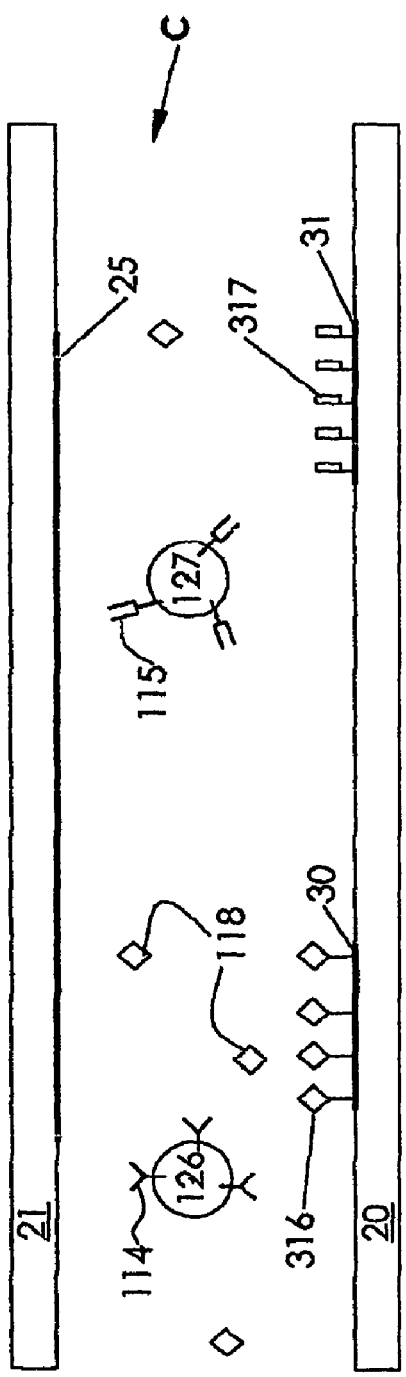
FIGS. 3A and 3B are schematic illustrations of a third embodiment of the instrument of this invention including an electrode that has at least one electrical property in a detection circuit that (a) does no t change because the analyte attaches to the agent on the electrically readable particles and (b) that changes in the absence of the analyte due to the agent on the electrically readable particle binding to the analog of the analyte on the electrode.
Figure 3B:
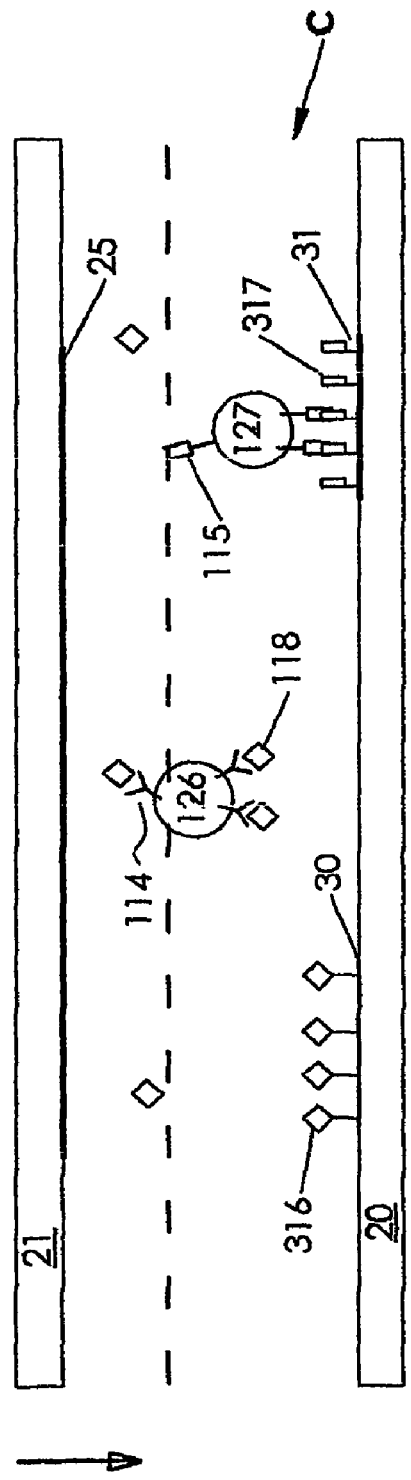

In FIGS. 3A and 3B, a competitive or inhibitory assay is illustrated using a third embodiment of this invention, the instrument C. The instrument C is similar to that shown in FIG. 1, but the housing 21a and motor M and drive mechanism D are not shown. In this third embodiment, analogs of analytes 316 and 317 are attached respectively to the surfaces of the electrodes 30 and 31, respectively. In the presence of the analyte 118 in the sample, binding to the electrically readable particle 126 is diminished. Failure of the particle 126 to bind to the first assay site due to the presence of the analyte 118 is a n indication that the analyte 118 is in the sample and the lack of binding will be detected by a detection circuit. In contrast, the particle 127 is bound to the analog 317 on the electrode 31 at the second assay site.

Figure 3C:
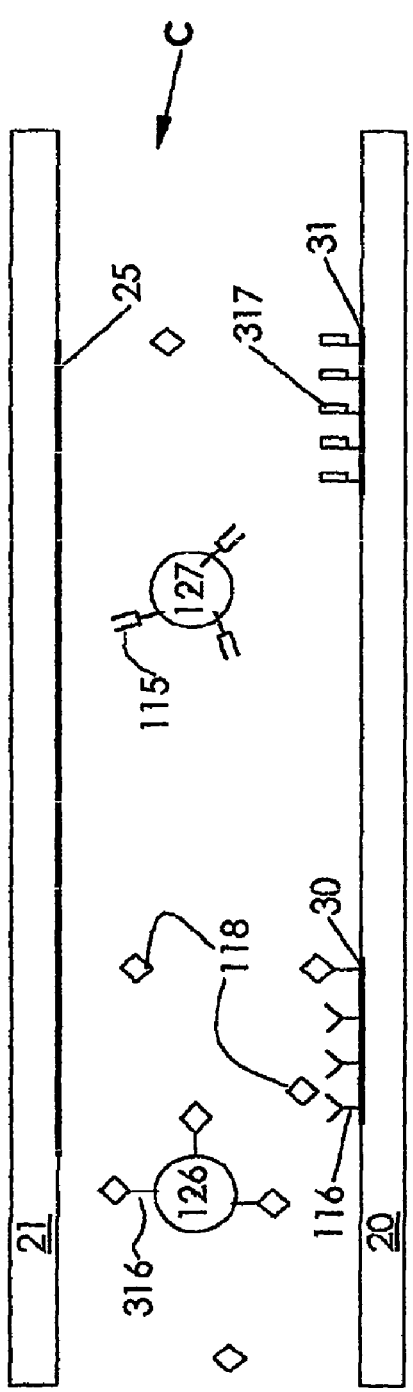
FIGS. 3C and 3D are schematic illustrations of another version of the third embodiment of the instrument of this invention where an analog of the analyte is bound to the particle.
Figure 3D:
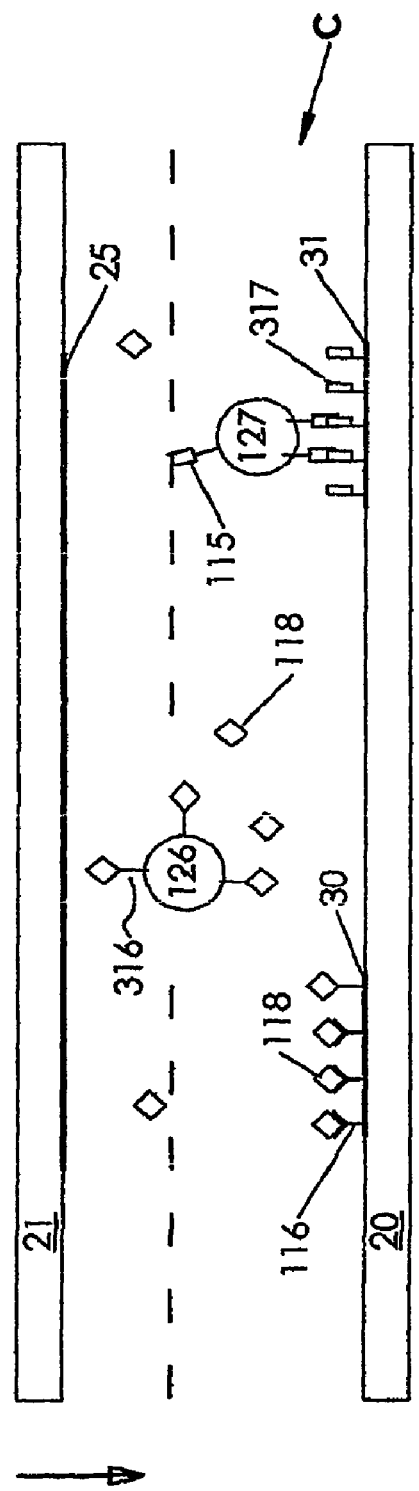

FIGS. 3C and 3D depict the particle 126 with the analog of the analyte 316 on the surface of the particle and the binding agents 116 on the electrode 30. In this case, when the electrodes 25 and 30 are moved from the spaced apart position shown in FIG. 3C into close proximity as shown in FIG. 3D, the analyte 118 does not bind to the particle 126, but will bind to the binding agents 116 on the electrode 30. T he detection circuit detects the absence on the electrode 30 of the particle 126 having thereon the attached analyte 118.

Fourth Embodiment

Figure 4:
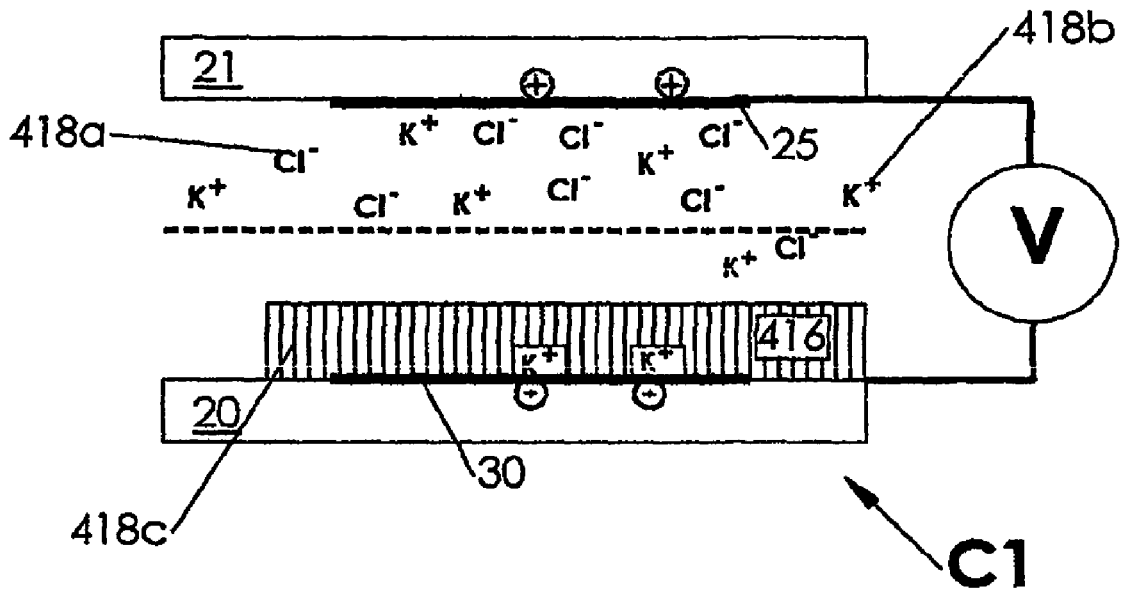
FIG. 4 is a schematic illustration of the fourth embodiment of the invention showing an assay site for detecting electrolytes.
Figure 5:
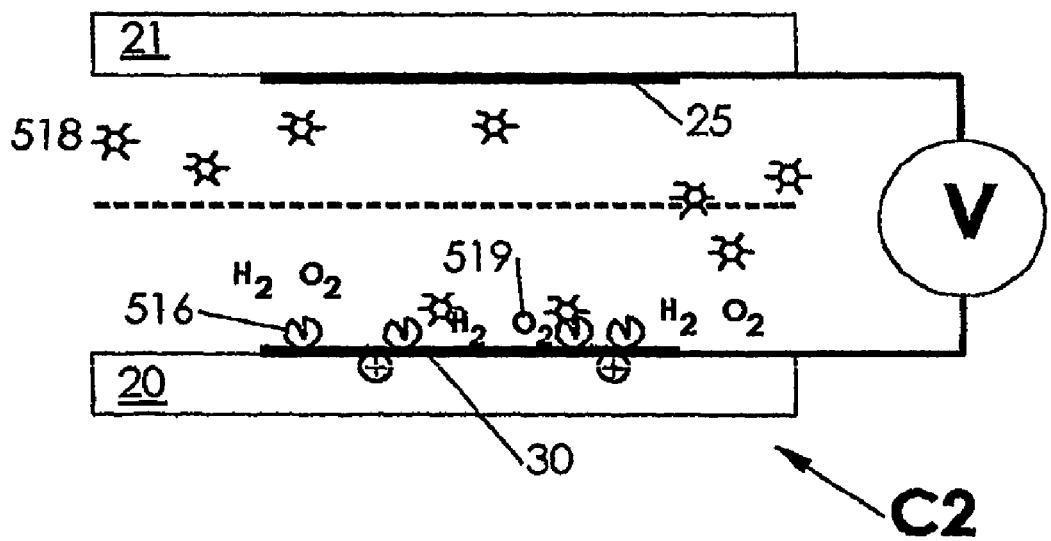
FIG. 5 is a schematic illustration of another version of the fourth embodiment of the invention showing an assay site for detecting small molecules such as glucose.

As shown in FIGS. 4 and 5, electrolytes and small molecules, are assayed using Case II embodiments of this invention. FIG. 4 depicts an instrument C1 for assaying a specific electrolyte, and FIG. 5 depicts an instrument C2 for assaying a specific small molecule. In FIG. 4 the electrode 30 has on its surface a membrane 418c can only be penetrated due to osmosis by potassium ions (K+) 418b. Other ions present such as the chloride ion (Cl−) 418a can not penetrate this membrane 418c. This is known technology. In accordance with this invention, the electrodes 25 and 30 are initially spaced widely apart as shown in solid lines. After sufficient time has elapsed to establish an ion current created by the movement of the potassium ions (K+) 418b and chloride ions (Cl−) 418a, respectively to the electrodes 30 and 25 due to the electrodes' opposite polarities, the electrodes are moved together into the position shown in dotted lines to suppress this ion current.

As depicted in FIG. 5, as is well known, a small molecule such as, for example, glucose 518, in the presence of hydrogen peroxide ($H_2O_2$) 519, will bind employ enzymes 516 to hold them to the surface of the electrode 20. In a similar manner as discussed in connection with the instrument C1, there is an ion current is first generated in the instrument C2, which ion current is suppressed by changing the position of the electrodes 21 and 21 from that shown in solid line to that shown in dotted lines.

Fifth Embodiment

Figure 6A:
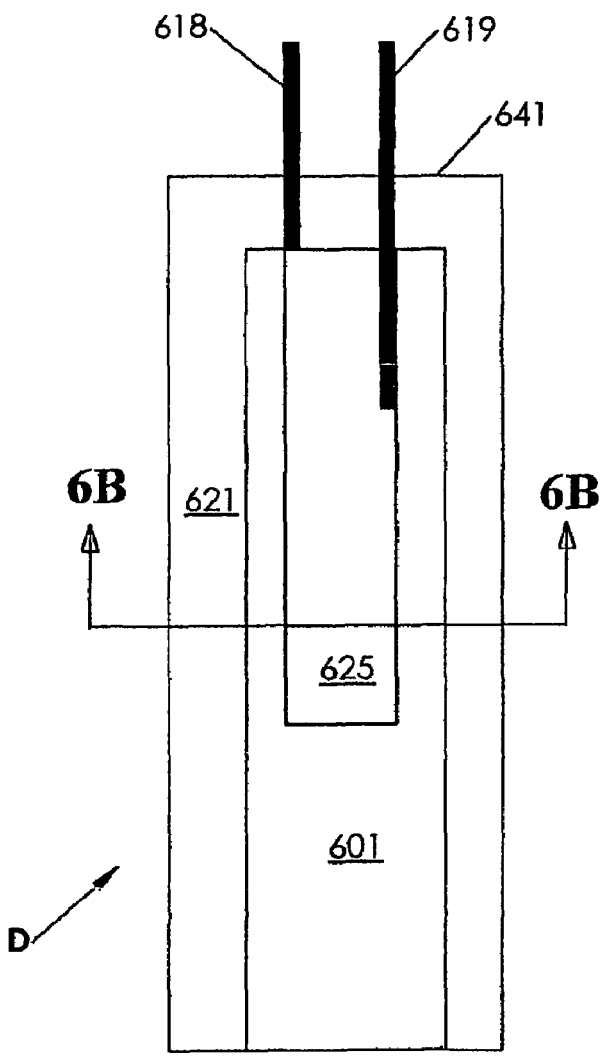
FIG. 6A is a schematic illustration of a fifth embodiment of the instrument of this invention shown in a plan view.
Figure 6B:
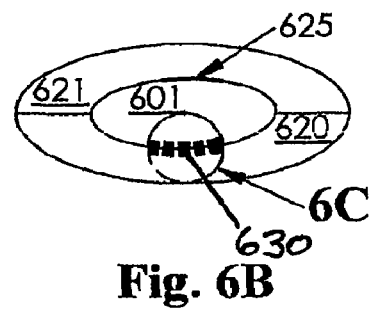
FIG. 6B is a cross-sectional view taken along line 6B-6B of FIG. 6A showing a capillary structure in an open position.
Figure 6C:
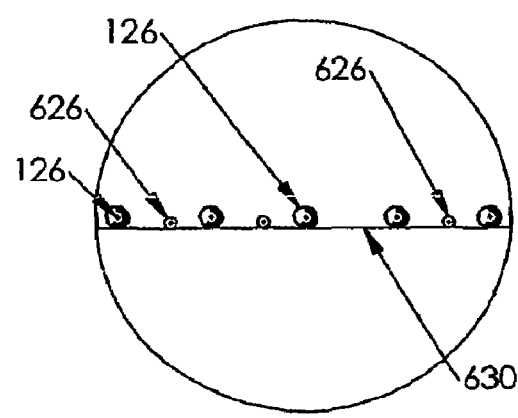
FIG. 6C is an enlarged fragmentary view taken along line 6C of FIG. 6B.

As illustrated in FIGS. 6A-6C, 7A and 7B, and 8A and 8B a n instrument D using a capillary tube 641 to move a pair of electrodes 625 and 630 between open and closed positions. This capillary tube 641 has upper and lower halves 620 and 621. The upper half 620 carries on its inside surface the one electrode 625. The lower half 620 carries on its inside surface the other electrode 630. As shown in FIG. 6B, the two halves 621 and 620, when separated as shown, provide a channel 601 through the capillary tube 641. Typically, the channel 601 has a diameter of from about 10 micrometers to about 10 millimeters. The tube 641 is preferably made of a plastic such as, for example, polystyrene, polypropylene, a polyimide, or a polyflorocarbon such as Teflon™. Both electrodes 625 and 630 are parallel with the longitudinal axis of the capillary tube 641 and are essentially identical to the electrodes depicted in FIGS. 1A and 1B. The electrode 630 is coated with a binding agent as discussed previously in connection with FIGS. 1A and 1B, and also sparsely coated with insulator (plastic) spherical spacer beads or particles 626. These spacer particles 626 are of smaller diameter than the electrically readable particles 126 in the sample flowing through the capillary tube 641. Typically, the electrically readable particles 126 have a diameter at least 10 percent greater than the diameter of the spacer particles 626. For example, if the spacer particles 626 are 200 nanometers, the electrically readable particles 126 are 400 nanometers.

Figure 8A:
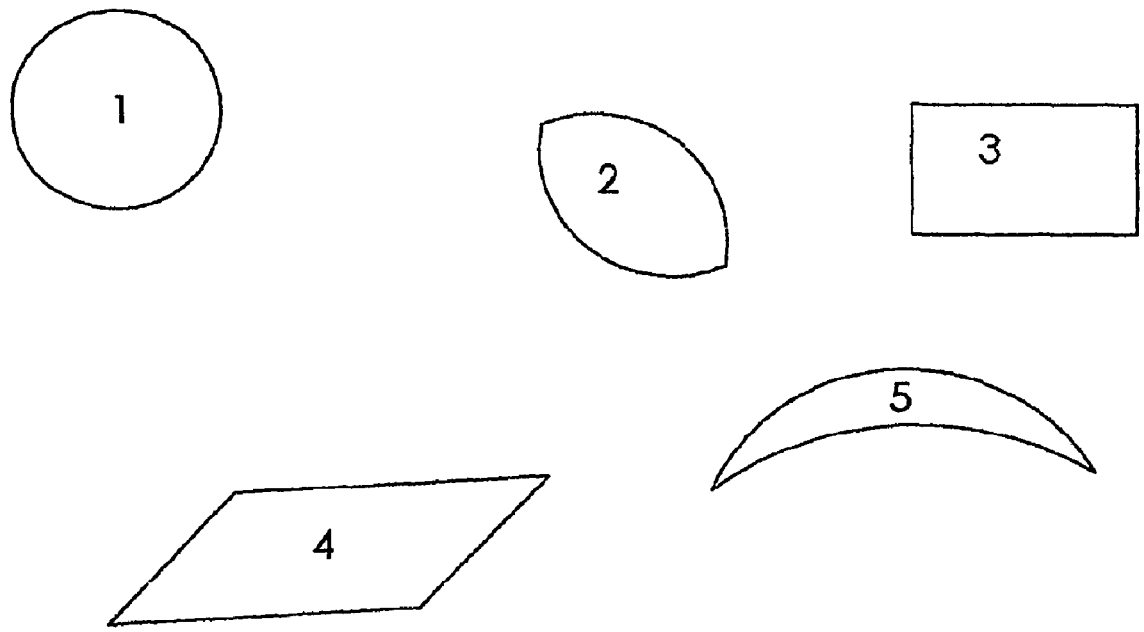
FIG. 8A shows cross-sections of different capillary structures.
Figure 8B:
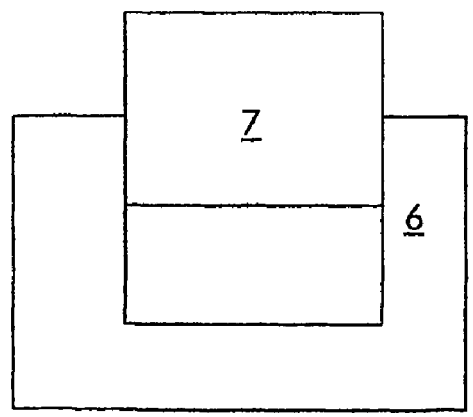
FIG. 8B is a cross-sectional view of a capillary structure with two separate walls, one being moveable relative to the other.

There are pins 618 and 619 respectively in the contact with the electrodes 625 and 630 for electrically connecting these electrodes in a detection circuit. The cross-sectional configuration of the channel 601 is oval. The capillary tube 641 may have cross-sectional configurations other than oval. As shown in FIG. 8A such other cross-sectional configurations are, for example, circular 1, eye-shaped 2, rectangular 3, rhombic 4, and crescent 5. As depicted in FIG. 8B, the capillary tube 641 may have two walls 6 and 7 that are moveable relative to each other.

The capillary tube 641 is made by bonding together the two similarly shaped halves 620 and 621, but the lower half 621 has a 250 nanometer (nm) deep and 200 μm wide longitudinal trench that is coated with a thin gold layer forming the electrode 630 in contact with the pin 618. The upper half 621 of the capillary tube 641 is also partially coated with a thin gold layer forming the electrode 625 in contact with the other pin 619. The electrode 621 is coated with binding agents 116 (FIG. 1A) and sparsely coated with 200 nm nonconductive spherical particles 626. The purpose of these particles 626 is to act as spacers that prevent the two electrodes 625 and 630 touching each other when the capillary tube 641 is compressed.

Figure 7A:
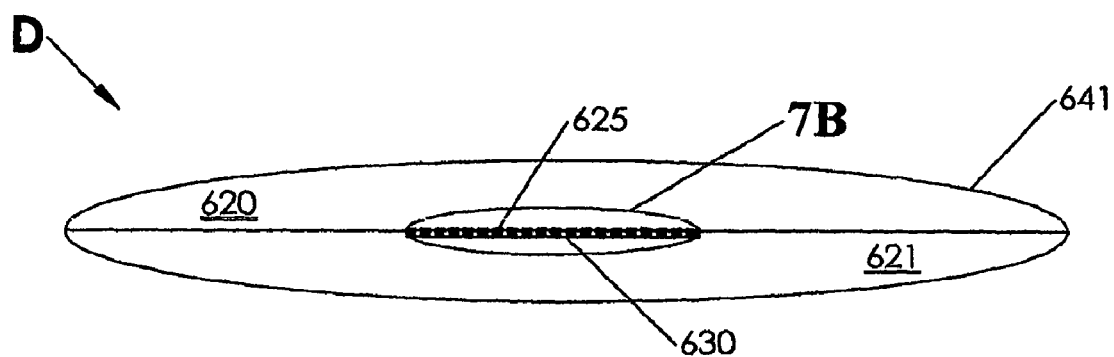
FIG. 7A is a cross-sectional view similar to that shown in FIG. 6B but with the capillary structure in a closed position.
Figure 7B:
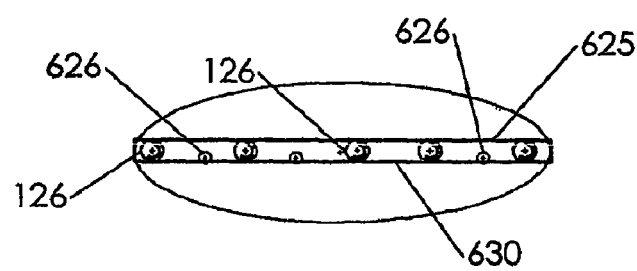
FIG. 7B is an enlarged fragmentary view taken along line 7A of FIG. 7.

When sample flows through the channel 601 capillary tube 641, it carries with it 250 nm gold particles 126 that are coated with the secondary binding agent 114. The number of the gold particles that are attached to the electrode 630 depends on the concentration of the analyte. The pins 618 and 619, for example, are in a detection circuit including an electric potential source. Any unbound gold particles 126 are washed away either with the sample or by a wash buffer. The capillary tube 641 is then compressed as shown in FIGS. 7A and 7B, so that both electrodes 625 and 630 are in contact with the particles 126. Because of the diameter of the gold particles 126 is greater than the diameter of the nonconductive spherical particles 626, an electrical property, in this case a current flow, is only produced when the gold particles 126 are present. A DC current will be directly proportional to the number of the bound gold particles. Due to the small distance between the electrodes 625 and 630 during compression of the capillary tube 641 any ionic current will be only transient, provided the potential is not too large to induce electrochemical reactions.

Many capillary tubes 641 may be assembled into an array. The height of the uncompressed channel 601 is more than the diameter of the electrically readable particles 126, that is, between 1 nm and 1 millimeter (mm), and preferably 10 nm and 3 micrometers (μm). The minimum width of the channel 601 is more than the width of an electrode, preferably at least 2 times the width of an electrode. The maximum width is less than a hundred times the width of the electrode 630, which is coated with the binding agent. The width of one electrode 625 or 630 varies, for example, between 100 nm and 10 mm. An array of capillary tubes 641 may contain up to 1000 electrodes. The large arrays tend to have smaller electrodes than small arrays. Thus, the total width occupied by an electrode, or an electrode array, is typically between 100 nm and 20 cm. The length of a capillary tube 641 depends on the number and type of various assays, and the accuracy that is required. The length varies between 100 μm and 1 meter (m), and is preferably 5 mm-50 mm.

Although in its simplest embodiment the present invention has no capillaries, or just one capillary, much more sophisticated microfluidic structures are possible. Reagents can be stored in cavities that are closed by a metal or plastic film that will be dissolved electrochemically just before the assay. The analytes can be fractionated by various chromatographic methods, including, affinity, size exclusion, ion exchange, adsorption, and reverse phase chromatographies. Electrophoresis is another well known technique for the separation of biomolecules. All these methods are well known in the art. Examples of microfluidic systems are: U.S. Pat. No. 4,426, 451 of Columbus, entitled Multi-Zoned Reaction Vessel Having pressure-Actuable Control Means Between Zones; U.S. Pat. No. 4,753,776 of Hillman et al, entitled Blood Separation Instrument Comprising A Filter And A Capillary Flow Pathway Exiting The Filter; U.S. Pat. No. 4,855,240 of Rosenstein et al, entitled Solid Phase Assay Employing Capillary Flow;

U.S. Pat. No. 4,963,498 of Hillman et al, entitled Capillary Flow Instrument; U.S. Pat. No. 5,304,487 of Wilding, entitled Fluid Handling In Mesoscale Analytical Instruments; U.S. Pat. No. 5,698,406 of Cathey et al, entitled Disposable Instrument In Diagnostic Assays; U.S. Pat. No. 5,798,215 of Cathey et al, entitled Instrument For Use In Analyte Detection Assays; U.S. Pat. No. 5,714,390 of Hallowitz et al, entitled Cartridge Test System For The Collection And Testing Of Blood In A Single Step.

An important part of the present invention is a movable electrode. In the preferred embodiment, at least two electrodes are inside the capillary tube 641, so that by applying a force the walls of the two halves 621 and 620 of the capillary tube come into close proximity. The capillary tube can be compressed to bring the electrodes 625 and 630 close to each other by many different means as discussed subsequently. In mass fabrication it is easier to evaporate or sputter the electrodes onto the inside surfaces of the halves 621 and 620 prior to bonding them together to form the capillary tube 641. One part is treated chemically to attach the binding molecules and then the two halves 621 and 620 are bonded together. However, by laminar etching techniques it is possible to perform etching inside a capillary tube and also to attach binding molecules. Although the bonding of two halves 621 and 620 is eliminated, this approach is relatively slow and is not currently preferred in mass production. Capillary tubes 641 can also be assembled from more than two parts. For example, each electrode and associated binding molecule can be deposited on a separate substrate. These are cut into flexible strips placed inside a capillary tube or assembled into arrays.

There is no absolute need to bond the recognition electrode and the movable electrode into one fixed capillary tube. The movable electrode can fit into a slot, in which it can slide and come into contact with the electrically readable particles. This is depicted in FIG. 8B. The contact surfaces between the two parts are preferably hydrophobic to prevent the leakage of the sample. If the sample volume is very high and not considered dangerous, the electrodes can be on an open surface. For example, when drinking or swimming water is tested, an open and relatively large area recognition electrode array is put inside water. After certain incubation time it is taken from the water and electrically readable particles 126 are added in suspension. After incubation, any unbound particles 126 are washed away, and the movable electrode array is brought into a close proximity and the measurement is performed. However, in clinical applications, capillary tubes are currently preferred in order to keep pathogens contained within them.

Many types of materials may be used in making the capillary tube 641, with the body of the halves 620 and 621 serving as substrates. If the halves 620 and 621 are not bonded together, there is no need for them to be deformable. If they are bonded into one structure as depicted in FIG. 6B, at least one half must be flexible. The materials are preferably non-conductors, although one half may be conducting. Accordingly, almost any material can be used, including but not limited to, metals, semiconductors, photoconductors, silicon oxide, ceramics, glass, rubber, plastics, such as polyethylene, polypropylene, polycarbonate, polyvinylchloride, polybutadiene, polystyrene, polyacetal, and silicone. This material may also be used in constructing the electrodes in any of the other embodiments disclosed. Substrates and patterning are discussed in the following references: U.S. Pat. Nos. 4,357,311; 4,886,761; 4,959,303; 5,514,501; 4,302,530; 4,562,157; and 5,413,732.

In FIG. 6B the capillary tube 641 is open. When the sample is drawn into this tube 641, the tube is compressed virtually into a closed state during the measurement. The situation can be reversed in the sense that the resting state of a capillary tube can be closed and it is expanded to be open during introduction of the sample. This approach has some advantages. First, the instrument acts like a Vacutainer™ (Becton Dickinson) with the difference that in this case the vacuum is created just before the sample is drawn. Second, because both surfaces can be flat, the fabrication is easier. A pre-drawn vacuum could be utilized, but it might affect the shelf life, and other variables.

Sixth Embodiment

Figure 9:
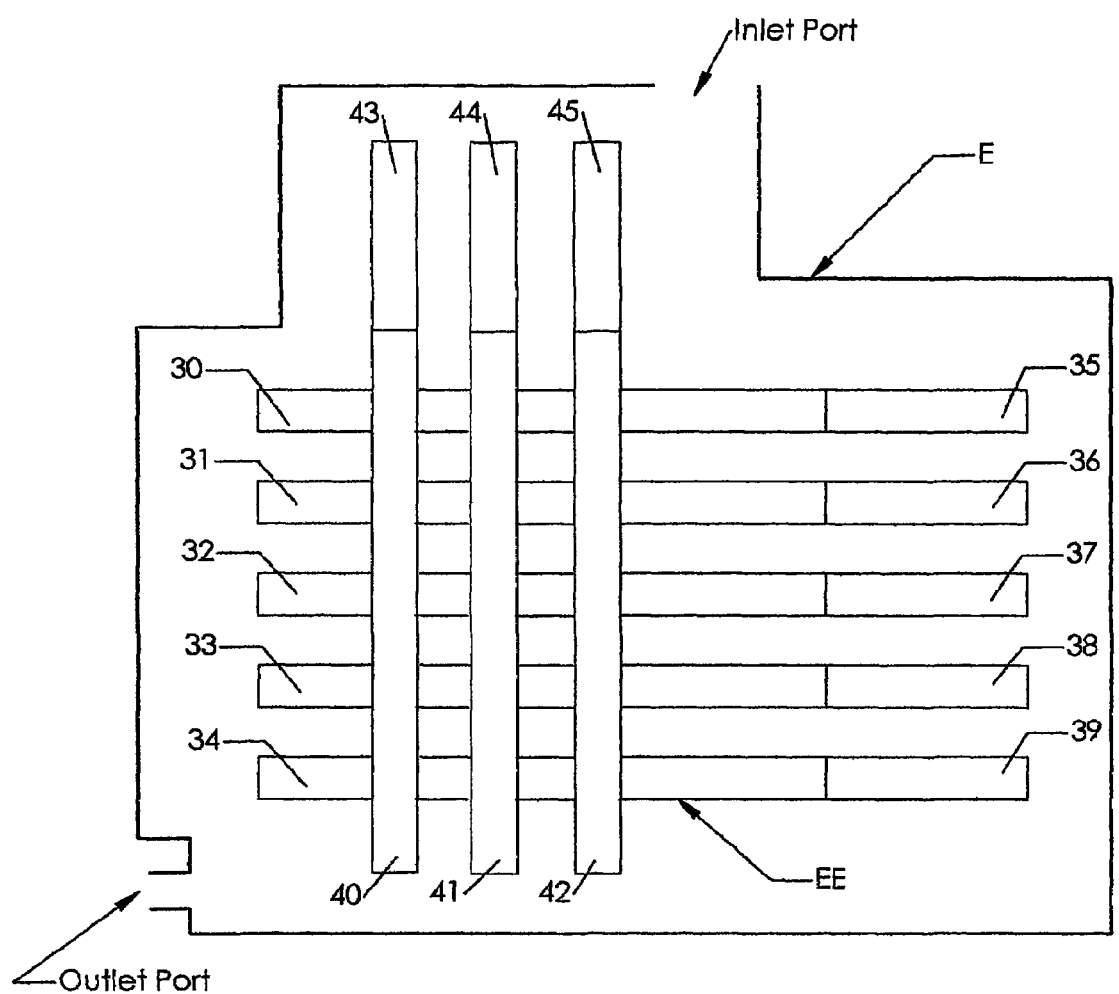
FIG. 9 is a plan view of a sixth embodiment of this invention employing a grid of overlying orthogonally oriented electrodes creating at the overlying intersections of the electrodes an array of test sites.
Figure 10:
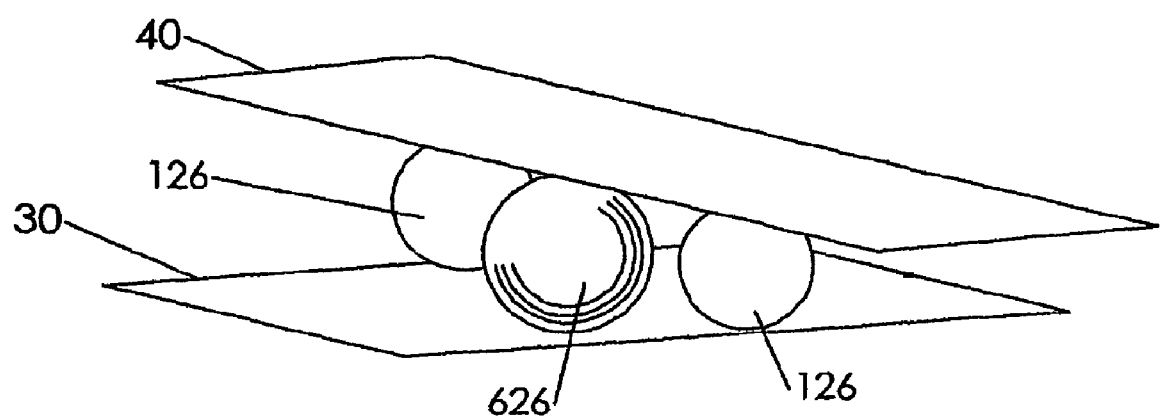
FIG. 10 is a perspective view of one of the test sites created the overlying orthogonally oriented electrodes shown in FIG. 9.

FIGS. 9 and 10 illustrate the sixth embodiment of this invention, an instrument E including inlet and outlet ports that allow a sample to flow past an electrode array EE. In this embodiment five electrodes 30-34 are supported on the surface of a lower insulator substrate as discussed in connection with FIGS. 11A through 11G and similar to that shown in FIG. 1A and three electrodes 40-42 are supported on the surface of an upper insulator substrate as discussed in connection with FIGS. 11A through 11G and similar to that shown in FIG. 1A. There are total fifteen intersections, which have coordinates (30,40), (30,41), (30,42), (31,40) . . . (34, 40), (34,41), and (34,42). A different assay can be performed in each intersection to detect different analytes. Binding agents specific to the analyte to be detected at an individual assay site are on the surfaces of the electrodes 30-34 at each site, and electrically readable particles 126 are in the sample being tested as discussed above. Preferably, spacer particles 626 are at each site as shown in FIG. 10.

Figure 11A:
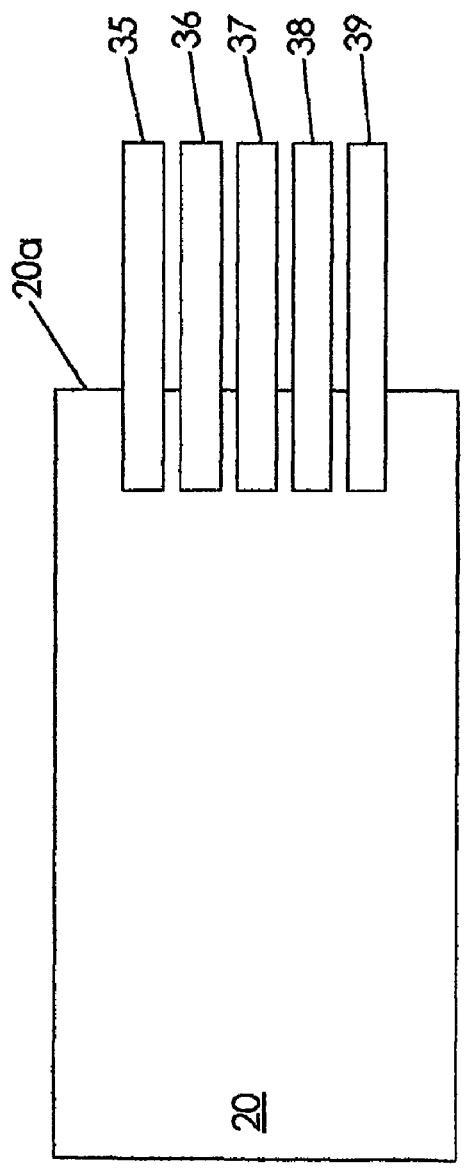
Figure 11B:
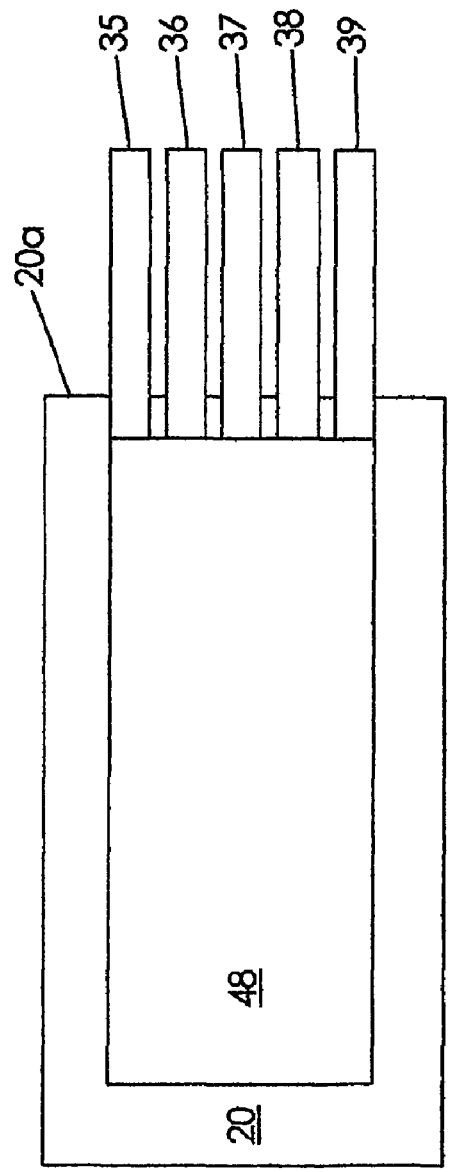
Figure 11C:
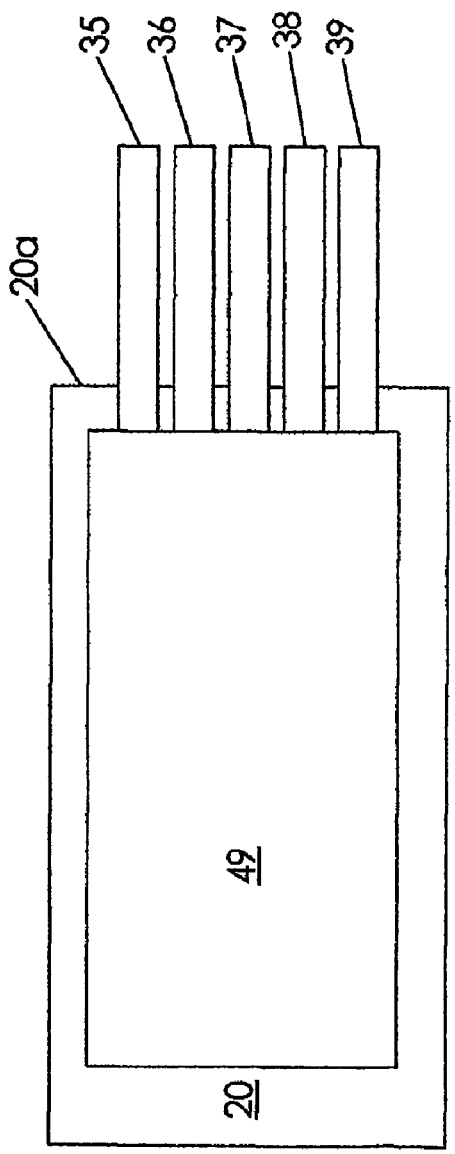
Figure 11D:
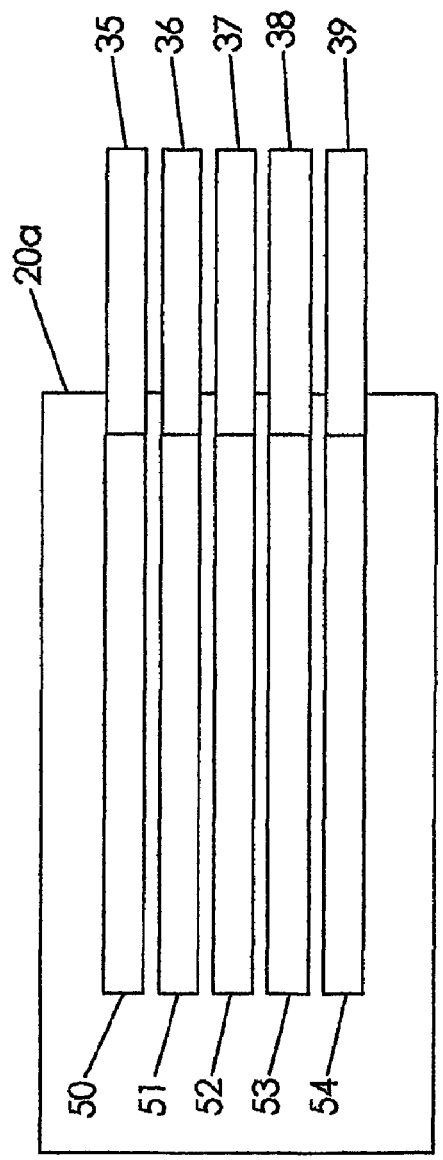
Figure 11G:
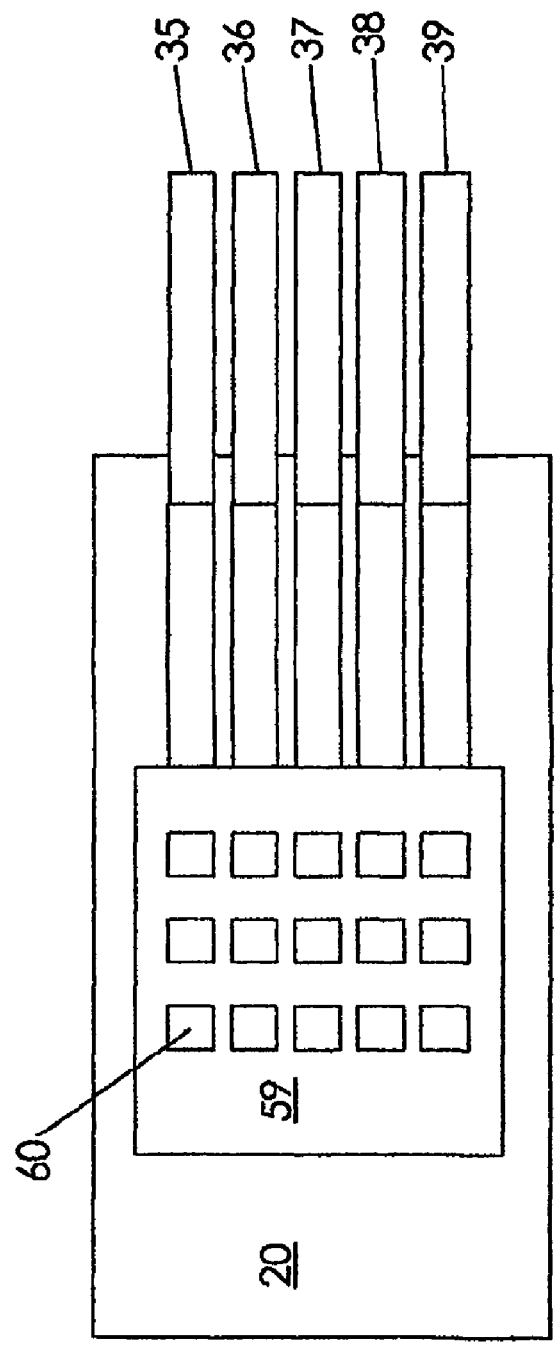

FIGS. 11A through 11G illustrate the manufacture of the electrode array shown in FIG. 9. Conventional manufacturing techniques are employed. As shown in FIG. 11B, an insulator substrate 20 with five pins 35-39 extending outward from an edge 20a of the substrate has a conductive layer 48 deposited of the substrate's surface so that electrical contact with pins 35-39 is established. As shown in FIG. 11C, the conductive layer 48 is covered with a photoresist 49. As shown in FIG. 11D, after illumination with ultraviolet light through a mask (not shown) extra photoresist 49 is removed, and electrode strips 50-54 are formed by etching away the exposed conductor 48. As shown in FIG. 11E, the remainder of the photoresist 49 is removed, and the electrodes 30-34 are exposed. As shown in FIG. 11F, the electrodes 30-34 are coated with another photoresist 55. As shown in FIG. 11G, the final pattern 59 is created illuminating through an appropriate mask and dissolving away the soluble part of the photoresist 55. This fabrication method gives an electrode array, in which the electrodes are exposed only in the intersections, thus creating the assay sites a t each intersection. In a simplified approach only steps shown in FIG. 11A through FIG. 11E are used.

FIG. 12 shows the electrode array illustrated in FIG. 9 having a holding electrode 61 in advance of the array. By alternating the electrical voltage applied to this electrode 61 electrically readable particles 126 being held to the surface of this electrode may be released and mixed with sample flowing through the instrument's inlet port (not shown). Before the electrodes at each assay site have been moved into close proximity with each other, the voltage applied to the holding electrode 61 is changed to remove unbound particles 126. The holding electrode 61 may be prepared exactly in the same way as discussed above in connection with FIGS. 11A through 11G.

Seventh Embodiment

Figure 13A:
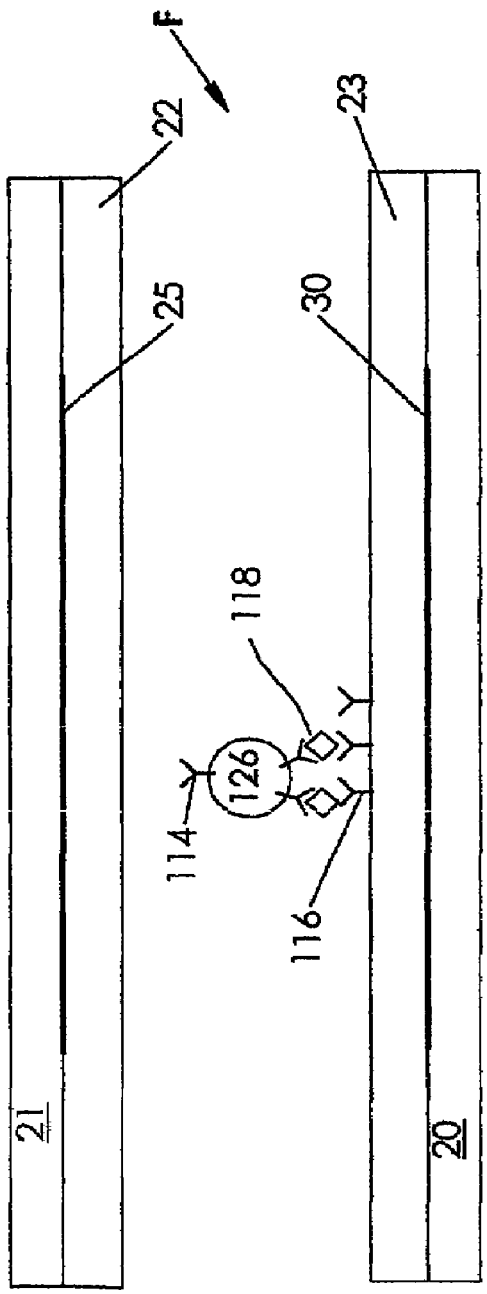
FIG. 13A is a cross-sectional view of a seventh embodiment of this invention schematically illustrating an instrument employing electrodes coated with a thin layer of soft material and the electrodes in an open position.
Figure 13B:
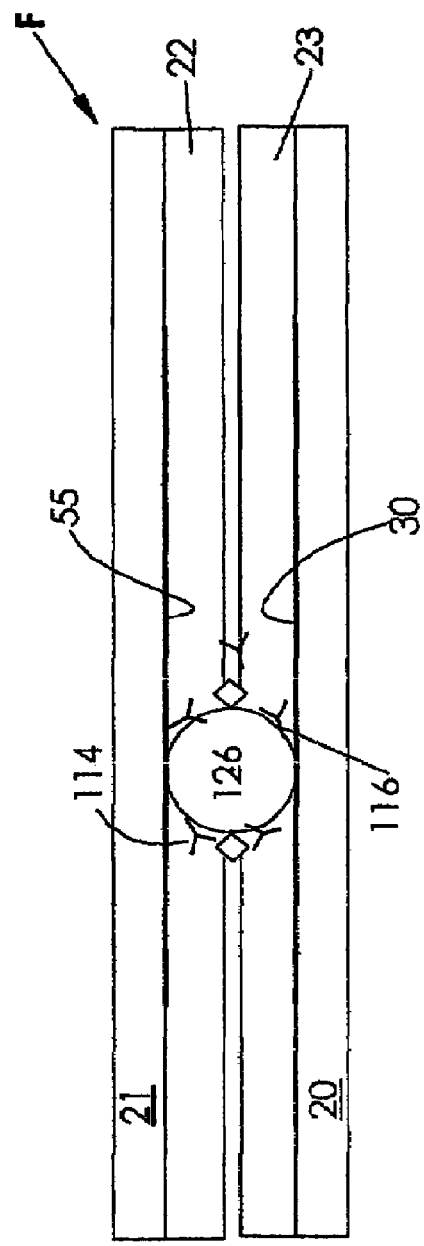
FIG. 13B is a cross-sectional view of the seventh embodiment of this invention schematically illustrating the instrument shown in FIG. 13A with the electrodes in a closed position.

As depicted in FIGS. 13A and 13B, a seventh embodiment of this invention, the instrument F, similar to the instrument A shown in FIG. 1A, employs the spaced apart electrodes 25 and 30. Each electrode has a thin layer 22 and 23, respectively, of soft material covering it. This soft material may be, for example, silicone plastic. The thickness of the soft layer should be about half diameter of the electrically readable particle 126, for example about 100 nanometers when using a electrically readable particle having a diameter of a little greater than 200 nanometers. The lower binding agent 116 is applied to the surface of the layer 23. Thus, in accordance with this invention, the binding agent 116 need not be applied directly to the surface of the lower electrode 30, but only be nearby this surface, or as expressed in the claims "thereat." When the electrodes 25 and 30 are moved from their widely spaced apart position as shown in FIG. 13A into close proximity with each other as shown in FIG. 13B, and pressure is applied to the electrodes, the particle 126 is pushed through the layers of 22 and 23 and binding occurs in the presence of the analyte 118, as discussed above. Thus, the layers 22 and 23 act as spacer elements.

Eighth Embodiment

Figure 14A:
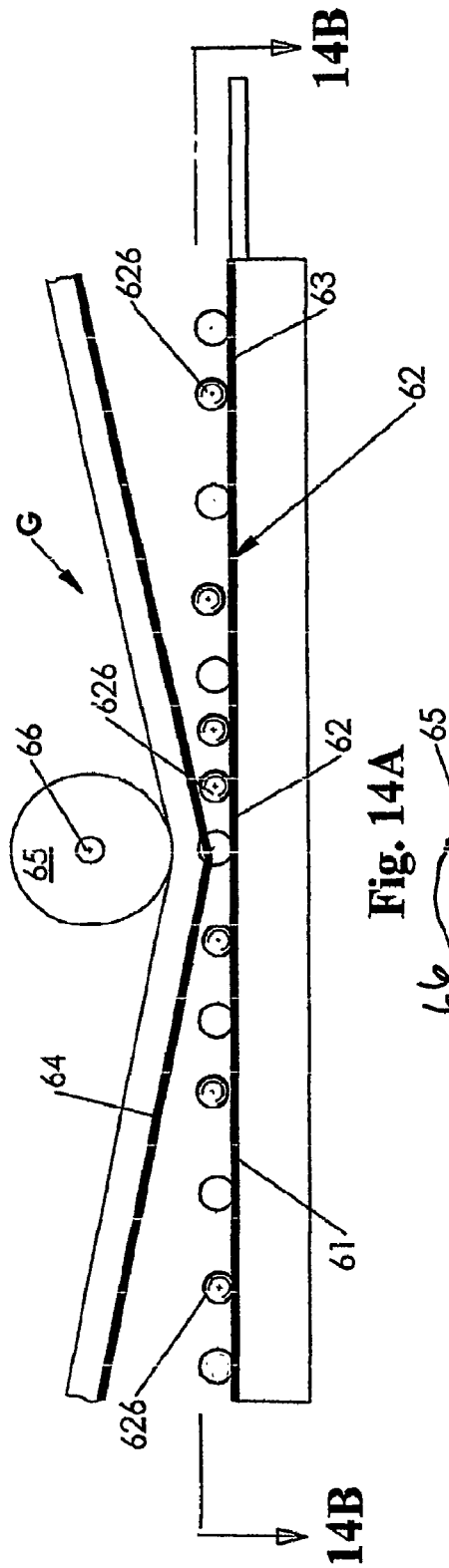
FIG. 14A is cross-sectional view of an eighth embodiment of this invention schematically illustrating the use of a flexible, resilient electrode.
Figure 14B:
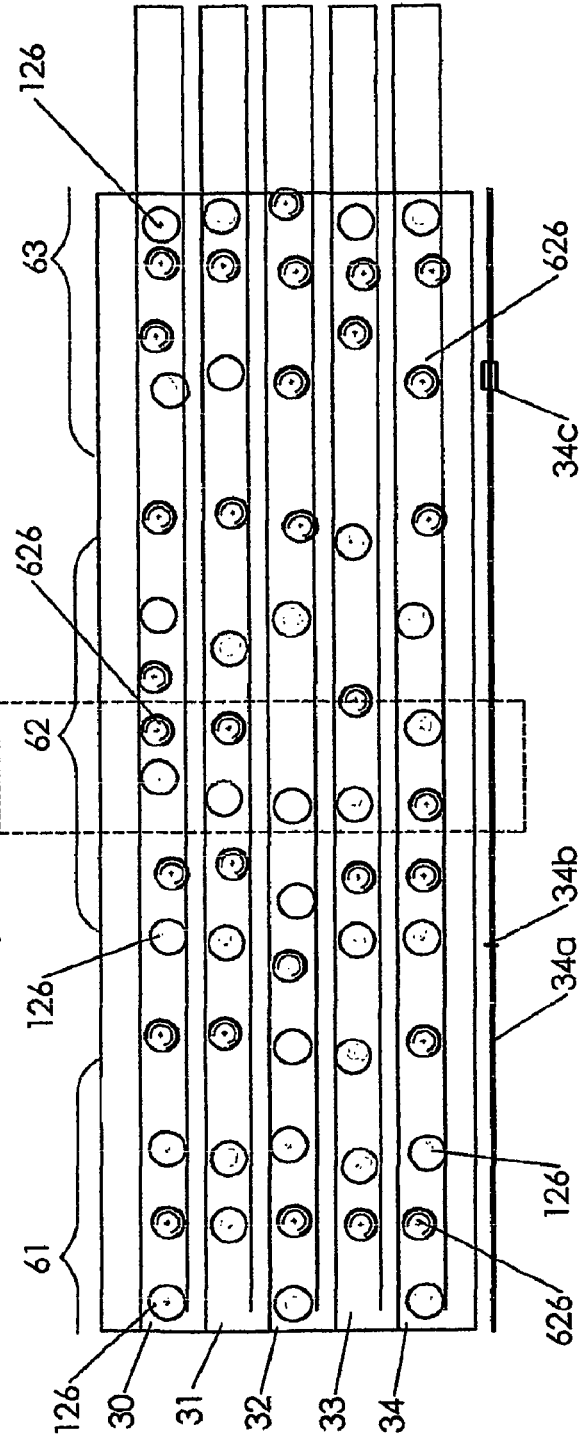
FIG. 14B is a plan view taken along line 14B-14B of FIG. 14A.

As illustrated in FIGS. 14A and 14B, a eighth embodiment of this invention, the instrument G, employs a roller 65 having its shaft 66 connected to a drive mechanism (not shown) that rolls the roller over three assay sites 61-63 sequentially, each site including pairs of electrodes. The upper electrode 64 is common to all three sites 61-63, and it is made of a flexible material, so that it bends as the roller 65 passes a site to move this electrode into close proximity to the lower electrodes 30 through 34 at any given site 61, 62, or 63. The roller 65, as shown in FIG. 14B, extends across all the lower electrodes 30 through 34, to which particles 126 are attached when analyte is present in a sample. A timing strip 34 is positioned along the path of travel of the roller 65, which engages markers 34a and 34b disposed in spaced apart positions along the timing strip to provide an electrical signal indicating the position of the roller relative the assay sites 61-63. Upon passing a site, the electrode 64, being resilient, returns to its widely spaced apart position.

Ninth Embodiment

The ninth embodiment of this invention, the instrument H, employs a ball electrode 73 between two electrodes 71 and 72, respectively on non-conductive substrates 21 and 20. Affinity bound electrically readable particles 126 are in wells 71a defined by a thin patterned spacer layer 59 of insulating material. The ball electrode 73, being conductive, will serve as an extension of the upper electrode, and in effect, constitutes moving a pair of electrodes between a first spaced apart position to a second position where the electrodes are in close proximity.

Tenth Embodiment

Figure 16A:
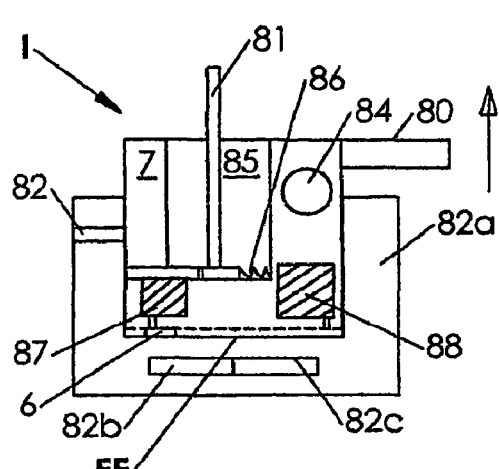
FIGS. 16A through 16D are cross-sectional views of a tenth embodiment of this invention schematically illustrating a hand held, single use, portable, disposable instrument with a needle that is extended to collect a sample of blood from a subject and retracted after collecting the sample.
Figure 16B:
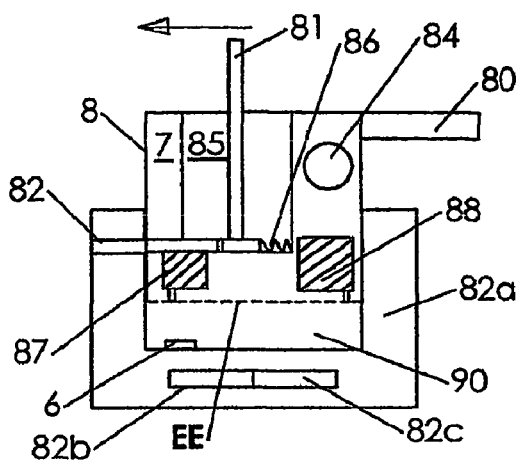
Figure 16C:
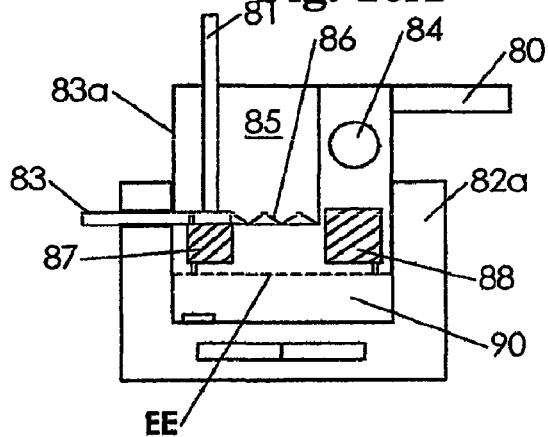
Figure 16D:
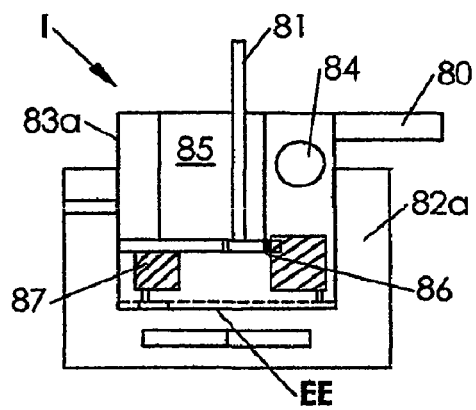
Figure 16E:
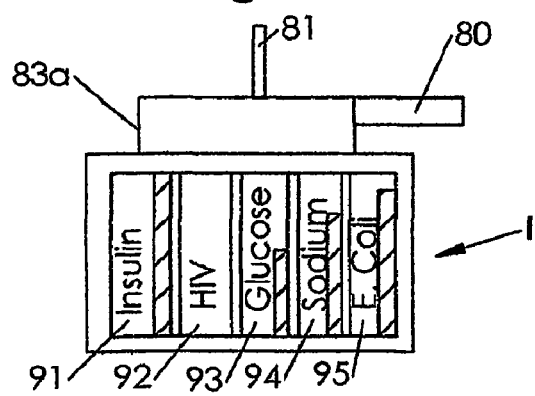
FIG. 16E is a plan view of the instrument shown in FIGS. 16A through 16D.

FIGS. 16A through 16B depict the tenth embodiment of this invention, a self-contained single use analyzer instrument I that is disposable and is hand held. This instrument I includes a housing 82a having a U-shaped cross-section with an orifice 82 in a side wall. Embedded within the base of the housing 82a are a microprocessor device 82b and memory device 82c used to control the operation of the instrument I. Seated within the housing 82a is a moveable block 83a holding a needle 83 that is manually moveable between a retracted position shown in FIG. 16A and a sample collection position shown in FIG. 16C. Within the block 83a is an electrode array EE providing a plurality of assay sites such as illustrated in FIG. 12, a battery 84, a filter 87 on the inlet side of the electrode array EE, and a pad 88 of absorbing material such as cotton. An external handle 80 attached to the block 83a is used to move manually the block from within the housing 82a as shown in FIGS. 16A and 16B to an outwardly extended position shown in FIG. 16C, and then return the block to the position shown in FIG. 16D. There is a lever 81 extending through the block 83a that is used to return manually the needle 83 to the position shown in FIG. 16D. This lever 81 has an internal end connected to the basal end of the needle 83 and an opposed end extending from the block 83a. A powerful spring 86 is coiled about the basal end of the needle 83 that force the needle through the orifice 82 when the needle is aligned with this orifice as shown in FIGS. 16B and 16C. A pellet 6 of sugar, or other water soluble bio-compatible material, containing the electrically readable particle 126 is positioned on the base of the housing 82a upstream of the array EE.

Figure 16F:
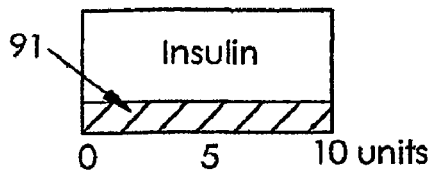
FIG. 16F is a plan view of a display on the instrument shown in FIGS. 16A through 16D providing a qualitative readout that a sample is positive for *E. Coli* in the sample and a quantitative readout indicating the amount present in the sample.

In FIG. 16A the instrument I is in a ready to use condition and the needle 83 is enclosed entirely within the housing 82a. First, the instrument I is pressed against the skin of the subject. When the block 83a is moved to the position shown in FIG. 16B by manual manipulation of the handle 80, a vacuum is created into a cavity 90 between the bottom of the block and the base of the housing 82a. The spring 86 rapidly pushes the needle 83 through the orifice 82 and into the subject's skin. Blood from the subject due to the vacuum flows into the instrument along a passageway that includes the pellet 6 and the array EE. The filter 87 removes any cells and other particles from the sample (this is optional). The block 83a is then manually pushed back into the housing 82a using the lever 81 to first withdraw the needle from the subject. The excess blood will be absorbed by pad 88. The cavity 90 as shown by shaded areas is filled with this blood and any analytes in the blood interact with the binding molecules and enzymes on the surface of the electrodes in the array EE. The holding electrode 61, under the control of the microprocessor 82b, has its voltage regulated to collect any unbound particles 126. Any change in the electrical properties of the intersections between the electrode arrays EE are measured. A display for different analytes 91-95 on the exterior of the housing 82a provides both a qualitative and quantitative readout if any one, or all, of these analytes is present in the blood sample. The instrument I is designed to detect all five classes of analytes: Class I proteins, Class II nucleotides such as, for example, RNA and DNA, Class III small molecules, Class IV electrolytes, Class V cell detection. Bars, numbers, colors, text etc. are used to report the result. FIG. 16F depicts, for example, the display indicating that the sample was positive for the *E. Coli* and the level in the sample namely 10 units.

Eleventh Embodiment

Figure 20:
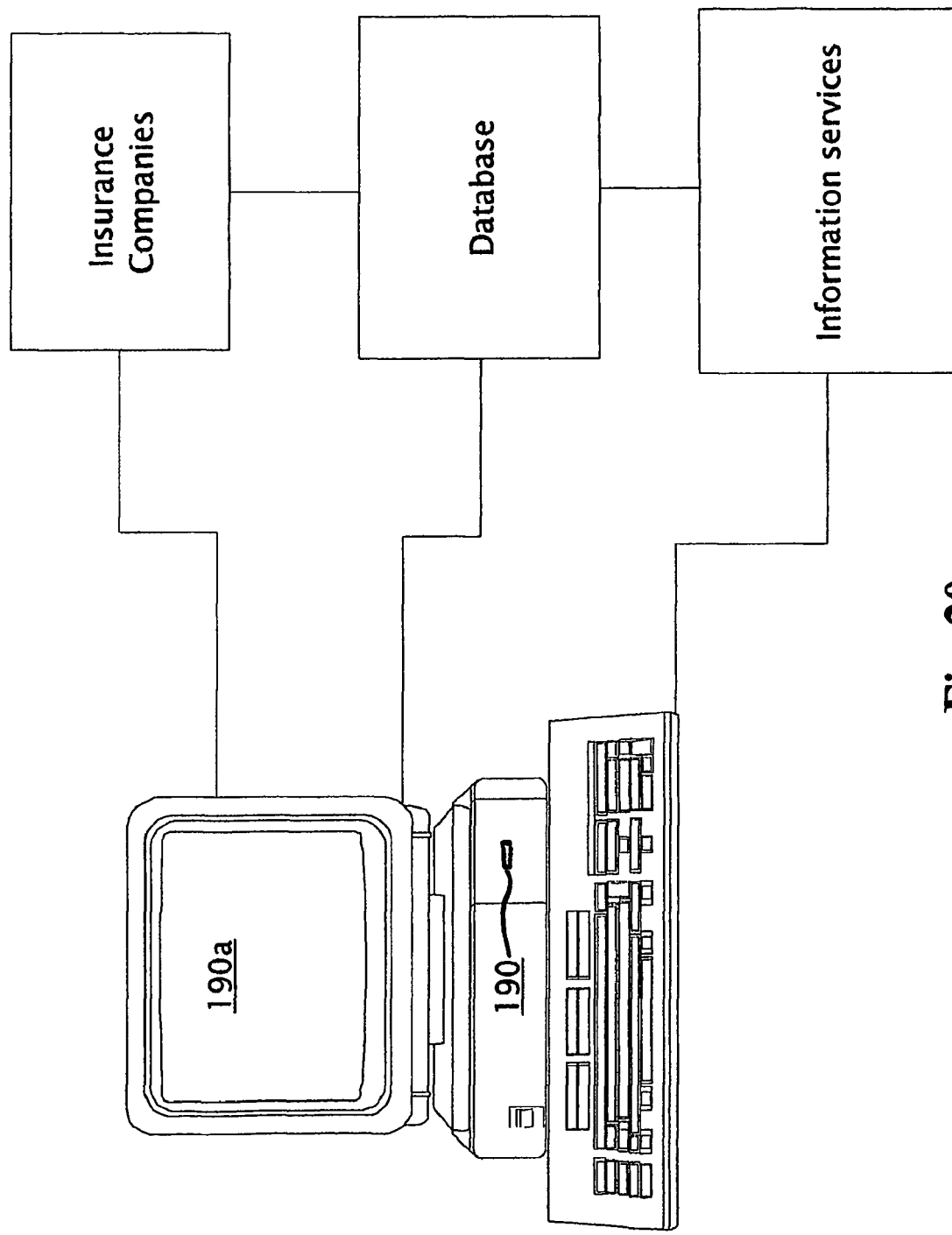
FIG. 20 is a schematic illustration of a computer network with the assembly of the disposable module and computer adapter shown in FIG. 19B being connected to the USB port in a computer.

The eleventh embodiment of this invention, the instrument J, shows a module 100a placed into an adapter 115a that is inserted into a USB port 190 of the personal computer shown in FIG. 20.

The module 100a is a hand held, disposable device similar in many respects to the instrument I, but designed to fit within the adapter 115a. It includes a needle 103 that is extended to collect a blood sample which flows past an array of electrode pairs, including the lower electrodes 100, 101, and 102 and an upper electrode 109 that is flexible and resilient similar to the electrode 64 used in the instrument G. The module 100a is shown with sample collected and the needle 103 withdrawn. Electrically readable particles 126 are shown adhering to the surface of the lower electrodes 100, 101, and 102 because of analytes present in the sample.

After collection of sample the module 100a is inserted into a adapter 115a that includes a roller 115 adapted to engage the electrode 109. The adapter 115a is compact, being shaped like a small box, so that it may be conveniently connected to the personal computer shown in FIG. 20. A drive mechanism 111a, including a screw 112 mounted between a pair of spaced supports 110 and 111 and a platform 114 support by another screw 113, serves to move the module 100a past the roller 115 and move the upper and lower electrodes from normally spaced apart positions into close proximity with each other sequentially like in the instrument G. A plug 117 makes an electrical connection with the computer through the electrical connectors 118 and 119 upon inserting the assembly of the adapter 115a and module 100a. Data that is gather corresponding to the presence or absence of analytes, and the amount, if any, present, is electronically transmitted, for example, over the internet, to insurance companies, a data base and other information services. This data may also be displayed on the monitor screen 190a of the computer.

Twelfth Embodiment

As depicted in FIGS. 21A through 21C and FIG. 22, the twelfth embodiment of this invention includes the instrument KA that is used with the detection system K. The system K automatically tests a series of sample containers 145 being moved in synchronization with a series of instruments KA. In the system K, a conveyor belt 140 moves the sample containers 145 past a rotatable collection member 140a having four radial arms 141-144. The collection member 140a and conveyor belt 140 are moved in a synchronous, step wise fashion, with each individual arm being positioned over each individual sample container 145 to draw the sample into an arm. A suction device (not shown) or other means is used to withdraw sample from a sample container 145.

Figure 22:
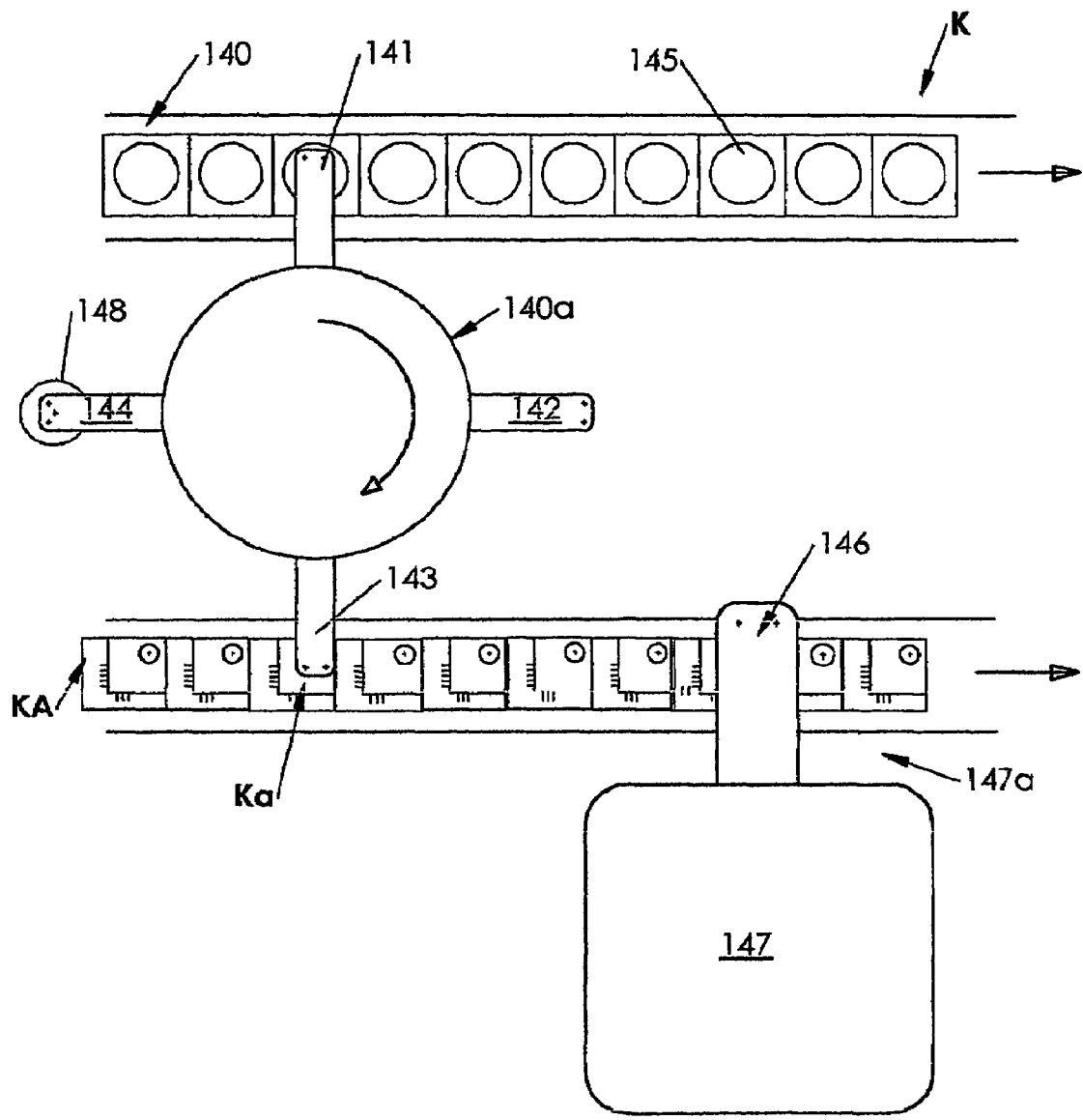
FIG. 22 is a plan view of an automatic detection system for testing numerous samples on a sustained basis over a prolonged period of time.

Another conveyor belt 140a is moved in a synchronous, step-wise fashion with the movement of the belt 140 and collection member 140a. This belt 140 carries the series of instruments KA embodying this invention such as discussed above, preferably having an array of orthogonal electrodes 40-42 and 30-34 supported on substrates 121 and 120. A holding electrode 131 is used in the same manner as discussed above to added electrically readable particles 126 to the sample and collect unbound particles by controlling the voltage applied to this electrode. As shown in FIG. 22, the belts 140 and 140a and the collection member 140a move synchronously so that sample is collected by one arm 141 and then previously a collected sample in arm 143 is fed into an inlet port 130 of one instrument Ka. A cleaning station 148 is position at about 9 o'clock to sterilize the arms 141-144 after they deposit sample in the instrument KA advancing to a readout station 147a that detects changes in electrical properties due to the presence of analytes in the individual samples being tested. The a readout station 147a includes a pressure application station 146 and a detection circuit and signaling device as discussed herein contained within a housing 147.

With the step-wise movement of the belt 140a, the individual instruments KA are advanced past the station 146 at which a force is applied against the array of electrodes in each individual instrument KA to move the electrodes from a spaced apart position into close proximity with each. Qualitative and quantitative readouts are provided by the a detection circuit and signaling device if any analyte in a sample is detected.

Electrically Readable Particles

Electrically readable particles can be made of the same materials as electrodes. Types of electrically readable particles include metal spheres, nano and microcrystals, plastic particles containing paramagnetic or magnetic material, carbon nano-tubes, metal nano-wires, piezoelectric particles, and conductive plastic particles. They can be and are preferably coated with a mono- or multilayer. The outer layer should consist at least partially of the binding molecules. Gold particles are currently preferred, because of their stability in water, and constant size particles ranging from 1 nm to 3 µm are commercially available. Also various coating techniques for gold, such as self-assembled monolayers, have been developed. Electrically readable particles can be composites of several materials. Plastic particles can be coated by a metal layer. Again gold is the preferred material.

In accordance with one aspect of this invention, the electrically readable particles are coated, at least partially, with the binding agent (recognition molecules). These recognition molecules are often charged. For example, oligonucleotides are negatively charged in all common buffers. A certain protein is negatively charged, if pH is above an isoelectric point and positively charged at lower pH. The charge is balanced by soluble counter ions, which form an electrical double layer. However, these particles move in an electric field electrophoretically. Also the particles repel each other because of ξ-potential. (J. N. Israelachvili "Intermolecular and Surface Forces", Academic Press, London, 1985).

Theory describes quantitatively the interaction charged colloidal particles. The charge of the electrically readable particles can be adjusted by attaching charged molecules, other than recognition molecules, onto the electrically readable particles. Examples of charged molecules are polylysine, polyasparagine acid, polyallylamine, polyacrylate, histone, and DNA. Oligonucleotides and DNA can be used to adjust the charge in immunoassays and also in DNA testing. In DNA tests the DNA that is used to regulate the charge must not contain a target sequence.

The charge may be regulated, for example, by pH, ionic strength, counter ions, solvent, and additives, such as polyethyleneglycol. Also the charged molecules may be attached on to the particles so that the binding is reversible. For example, if the surface of the particle is sparsely covered by negative moieties, such as carboxylates, an excess of a positive polymer, such as polyallylamine, will bind on to the surface and give the surface a positive charge. The negative charge of the carboxylates may be eliminated by adding acid so that pH is below 5. The binding of the positively charged polymer will be much weaker, and a significant part or possibly all of it will be detached from the particles. It is also possible to change the charge by a chemical reaction. For example, the positive charge of amino groups can be eliminated by acylation that is conveniently done in water by active esters, such as acyl N-hydroxysuccinimides.

Electrically readable particles may also be charged with static electricity, which may purposefully adjusted to be either positive or negative. The charge may also be changed during the assay. An additional charging electrode may be added to give the particles a charge before they enter into the assay area.

The charge of the particles can be utilized in many ways in assays. First, the particles may be forced to move through the sample electrophoretically, and while they are moving their recognition molecules will interact with the sample and collect analyte molecules. Second, the particles can be attracted on to the surface of one electrode. By alternating the charge of two electrodes that define one intersection, the particles can be concentrated on to that intersection. The binding kinetics of the particles will be much faster because of the concentration and the physical contact induced by the electric field. Third, by removing the particles by a reversed electric field, or by attracting the particles to another intersection, or by changing the charge of the particles, the strength of the analyte mediated binding can be measured. This is important to test the specificity of the binding. Specific and non-specific binding in immunoassays can be differentiated. Moreover, the binding force can be measured. In DNA tests this allows differentiation between SNPs (Single Nucleotide Polymorphisms). Fourth, the charge of the particle can be adjusted independently of an analyte. The charge can be even opposite to that of an analyte. For example, DNA binding particles may be made positively charged. After interacting with a sample these particles can be attracted on to the negative electrode surface. The soluble DNA in the sample as well as DNA that is weakly bound on to the particles would be repelled from the electrode.

Although the electric charge of an analyte has been used earlier to attract and remove the analyte from an electrode, the present method is fundamentally different in several aspects. In this context the important difference is that the charge of the particle, and not the charge of an analyte, is the decisive factor. Also the whole electrode structure, and function as well as the detection method are significantly different from earlier approaches. All these aspects are discussed above in their appropriate context.

Electrodes

Although gold is currently preferred as an electrode material, many other conductive, semiconductive, magnetic, or piezoelectric materials are possible. Examples include platinum, palladium, osmium, iridium, silver, chromium, vanadium, tungsten, copper, nickel, graphite, semiconductors, such as silicon, germanium, zinc sulfide and selenide and conductive compounds and plastics, such as polyaniline, polyacetylene, polythiophene, and polyphenylene, tetrathiofulvalene, tetracyanoquinodimethane and their derivatives. Corrosion of an electrode prevents the use of some metals like iron and aluminum. Amalgams and composite materials are often more corrosion resistant, durable, and/or conductive than any pure component alone. Example is boron doped silver, several semiconductors, and carbon composites. If an electrode is coated by a thin protective layer, such as fatty acid monolayer, almost any metal can be used including iron and aluminum. This layer can be also conductive, for example, it can be gold, amorphous carbon, graphite, fullerene, tantalum nitride, tetrathiophene carboxylic acid, redox protein, such as cytochrome c, cytochrome c oxidase, or horse radish peroxidase. Electric current c an flow across thin insulating layers by tunneling, and accordingly conductivity is not mandatory. Also when electrodes are brought into close proximity and compressed, the electrically readable particles can penetrate through a thin insulating layer. After the electrically readable particles have been bound onto the electrode, it is possible to add a solvent that is able to remove the insulating layer, or enzymatically remove compounds such as carbohydrates, proteins, lipids, or nucleic acids.

The direct contact between the electrodes and electrically readable particles is not mandatory. Some electrical properties, for example capacitance, is modified by the presence of electrically readable particles between electrodes. Moreover, electric field is locally increased at the point in which electrically readable particles are located. Accordingly, chemical or electrical plating starts preferentially at these points. These plating methods can create an electrically conductive path between electrodes.

Electrode arrays are advantageously parallel stripes. By orienting two such arrays orthogonally, one with M and the other with N stripes, there are a total of M×N intersections (FIG. 12). The electrical properties of each intersection can be independently measured. These electrical properties include conductance, resistance, inductance, and capacitance. All of these can be correlated with the number of electrically readable particles in that specific intersection. The number of particles depends on the concentration of the analyte that is bound by the specific binding molecules in that intersection. Thus, the concentration of each of M×N analytes can be correlated with the electrical properties of the corresponding intersection.

Electrodes can be in shallow trenches. The depth of a trench should be about the same as the size of the electrically readable particle. Alternatively, electrodes can be separated by ridges that have about the same height as the diameter of the electrically readable particle. Instead or in addition to ridges, hillocks can be a part of the structure. The purpose of these structures is to prevent direct contact of two electrode surfaces. A third way to avoid the direct contact is to use non-conductive particles as spacers. Also any combination of these methods can be used spacers.

Still another method is to coat the counter electrode or electrode array with an essentially uniform layer of a soft material. Examples of such materials are silicone, vasoline, a mixture of triglycerides, and polyvinyl alcohol. When the electrodes are compressed into a close proximity, the spacer layer prevents direct contact between the electrodes, but the conductive particles will be able to penetrate through the spacer layer. This method has a further advantage that the space between the electrodes is essentially filled with a non-conductor.

Also any combination of the above methods may be used.

In a instrument having one roller (FIGS. 14A and 14B) only one electrode needs to be patterned consisting of an array of $N^{1/2}$ electrodes for N analytes. On the other side is only one electrode that is about the same size as the whole counter electrode array. Registration can be maintained by controlling the position of the roller. It is also possible to add location electrodes into the array. These additional electrodes would contain location and other information, such as the type of the assay, in the form of the bar code that is read when a roller presses a counter electrode against them. The intersections are defined by the patterned electrodes and a roller. Only two electrodes are needed even for very large arrays with two orthogonal rollers, which in a preferred embodiment are orthogonal, but may be in any non-parallel orientation. The other roller would be under the lower substrate in FIGS. 14A and 14B parallel to the surface of the paper. In the example depicted in Fig. FIGS. 14A and 14B the roller presses one substrate. The electrode or electrode array can be directly on the surface of the roller. If two rollers, are used, only one electrode on each roller is needed even for millions of assays. The contact point between two rollers defines the assay site.

In another embodiment of the present invention, a conductive ball 73 forms a counter electrode (FIGS. 15A, 15B, and 15C). This ball 73 should be at least ten times larger than the electrically readable particles 126 bound by affinity binding, and preferably they are macroscopic in the range of 0.1 mm to 50 mm, most advantageously between 1 mm and 5 mm. The contact point between the ball electrode 73 and the affinity electrode is the assay site. No patterning of the electrode is required, although patterning is still possible. Especially the surface can have a texture that controls the contact force and area.

In the preferred embodiments, the electrode is nonporous and flat. However, porous and textured electrodes have some merits. Grids, such as electron microscopy grids, allow a sample to flow through an electrode. This will increase the contact between the electrode and sample. Moreover, the electrodes are not necessarily rectangularly shaped. The areas containing binding agents (recognition molecules) may be enlarged or contracted. Also electrodes may be curved so that they diverge to allow easier contact with the outside macroscopic world.

The area of the intersection defined by two electrodes depends on the type and requirements of the assay. Qualitative assays may need only a very small area. It might be enough to bind ten electrically readable particles to achieve a reliable qualitative result. For a quantitative assay the minimum number of particles is about 100 otherwise the result is not reliable. For optimal accuracy the number particles should be about 10,000. This means that in a preferred embodiment the area of the intersection should be between 50 $\mu m \times 50$ $\mu m$ and 500 $\mu m \times 500$ $\mu m$. With the present invention it is possible to assay simultaneously 100 or even 10,000 analytes.

The present invention is in most embodiments a small instrument. It is possible to fabricate a really microscopic instrument that has the capability to measure multiple analytes. For example, microscopic forceps can be partially coated with metal. A part of this metal is further coated with binding molecules. An array of these modified forceps can perform multiple assays. The array can be inside a capillary tube, which can be so small that it can be used intravenously.

The instrument of the present invention can be manufactured by several means. In mass production, molding is a preferred method. Machining, laser, and water jet cutting may sometimes be advantageous. FIGS. 11A through 11G depicts a photolithographic method, in which the second resist layer 59 defines wells 60 and also acts as a spacer. This method is amenable to small scale production. Methods that are better for mass production are given in Examples 1 and 2. Electrodes can also printed by screen-printing technology. For example, commercially available carbon ink paste and silver/silver chloride ink are suitable materials for working, counter, and reference electrodes. Other printing or stamping techniques, such as ink jet printing can be used.

The means for moving the electrodes from a spart apart to a close position included, but are not limited to, mechanical, hydraulic, electromagnetic devices. This movement may be induced by a spring, screw, liquid or gas pressure in a closed container, thermally induced expansion of the compressing part, solenoid, or piezo crystal (U.S. Pat. No. 4,874,979) to mention the most important means. Moreover, compression may be achieved manually using a hand directly, or indirectly. Indirect compression may be induced by forcing the instrument into a constrained space, in which the walls of the space force the capillary tube 641 to deform.

Attachment of Recognition Molecules onto the Electrodes

Binding agents, that is recognition molecules, can be bonded onto the surfaces by physical or chemical means. When a voltage, resistance, or current across an electrode intersection is to be measured, the electrically readable particles should be as close as possible to the electrodes. Accordingly, the recognition molecules should be either bonded directly onto the surface or connected with relatively short spacers. Electric current can easily flow over a thin monolayer by a tunneling mechanism. Longer spacers can be used, if they are electrically conductive. For instance, double helical oligonucleotides are electrically conductive and can be used as spacers. Compounds like tetrathiophene carboxylic acid are also conductive enough to be useful spacers. Small electrically readable particles, such as 1-100 nm gold spheres can be coated with recognition molecules and bound with the surface. The same or even better result can be achieved by having an electrode surface that has 1-100 nm roughness. Currently 10-20 nm surface roughness is preferred. A sputtered metal surface has typically this kind of roughness. Sharp edges and vertices are advantageous, because these will penetrate any spacer and layer of recognition molecules and create a direct electrical contact between the electrodes and the electrically readable particles.

Although metal surfaces are often polycrystalline, single crystal surfaces may sometimes be preferable. For instance, pyridine has highest affinity for a (210) gold surface of all possible gold surfaces, while it has the lowest affinity for a (111) gold surface. In general, positively charged surfaces have higher affinity for electrically neutral molecules than negatively charged surfaces. The problem with high positive potential is that some important classes of compounds, such as mercapto compounds, will be oxidized and detached from the surface.

Spacers, recognition and other molecules can be bonded onto the surface by dispersion forces, hydrophobic force, hydrogen bonds, charge transfer, ionic or covalent bonds. Covalent bonds are strongest and most stable in hydrated milieu. Dispersion forces, such as van der Waals force, can be significant if a molecule is large and has tens of interactions, which combined can be comparable to a covalent bond.

Binding molecules can be adsorbed either from gaseous or liquid phase onto the surface. Laser ablation allows the evaporation of quite large molecules, such as peptides and oligonucleotides. However, proteins and oligonucleotides are preferably adsorbed from a buffer. Mercapto, amino, isonitrilo, carbonyl and carboxylate groups form bonds with various metals. Sulfur atoms interact especially strongly with gold and also with other noble metals. Organic mercapto compounds can also be dissolved into organic solvents, such as ethanol, and they will spontaneously form a self-assembled monolayer. Also ether oxygen binds with gold, although much more weakly than sulfur. Polymers containing many ether oxygens, such as polyethylene glycol will still bind strongly enough. Amphiphilic molecules form a monolayer at water-air interface. This monolayer can be compressed in a controlled way so that molecules occupy a desired average area. The monolayer can be deposited onto a solid surface such as a n electrode.

After the recognition and other molecules have been deposited, they may be surrounded by a liquid, liquid crystalline, or solid matrix (the pellet 6, FIG. 16A) to increase their stability. The matrix is preferably such that it will be dissolved by a sample. It is also possible to add a special buffer or some other solvent before or during the assay to expose the recognition molecules. Well known stabilizers are, for example, trehalose, glucose, glycine, glycerol, dextran, cyclodextran, starch, polyvinyl alcohol, and polyethylene glycol. Surfactants may be added to speed up the hydration. Surfactants include tween-20, octyl glucoside, sodium dodecyl sulfate, sodium palmitate, potassium oleate, sodium cholate, trimethyl octadecyl ammonium bromide, and phospholipids, such as dihexanoyl phosphatidyl choline, 1-palmitoyl-2-oleoyl-sn-3-phosphatidyl choline, and 1,2-dilinolenoyl-sn-3-phosphatidyl ethanolamine. Various salts, such as sodium chloride, sodium phosphate, sodium acetate, potassium lactate, sodium citrate, calcium chloride, and magnesium chloride, may be a part of the formulation. Combinations of these and other compounds can be used to reduce crystallization. These compounds are often solubilized into water, and the water solution is applied by a pipette, ink jet printer, or by pins on to the surface. Water is best removed by lyophilization.

Reagent patterning and stabilization for such testing are discussed in the following references: U.S. Pat. Nos. 3,572,400; 4,634,027; 4,216,245; 5,001,048; 5,554,339; 4,329,317; and 5,413,732; and J. Lipkowski and P. N. Ross, "Adsorption of Molecules at Metal Electrodes", VCH, New York, 1992.

Oligonucleotides may be terminated by amino, mercapto, biotinyl, and several other groups. There may be several amino or other groups as well as combinations of various groups. To give more freedom for oligonucleotides these groups, which are intended to bind with a substrate, can be separated from the actual oligonucleotide sequence with a spacer. Spacer is preferably water soluble polymer, such as polyethylene glycol, polyvinyl alcohol, polyacrylic acid, or optionally a copolymer of two or more hydrophilic and hydrophobic monomers.

Ionic and Electronic Current

Immediately after a potential is coupled over an electrode intersection that has electrically readable particles, there will both ionic and electronic current. The Nernst-Planck equation gives the flux of any ionic or molecular species in the electric field.

$$J_i(x,t) = -D_i \frac{fC_i(x,t)}{fx} - \frac{zFD_i}{RT}\frac{fC_i(x,t)}{fx} + V(x,t)C_i(x,t)$$

Each ionic species may have different diffusion constant $D_i$, charge $z_i$, and concentration $C_i(x,t)$. Each has an effect on the potential $\phi(x,t)$. Thus, an analytic solution is in most cases very difficult or even impossible and the equations must be solved numerically using a computer. The diffusion coefficient is usually between $10^{-5}$ and $10^{-6}$ cm$^2$/s. This means that the molecules and ions will diffuse from one electrode to another in a fraction of a second, because of very small distance between the electrodes, that is, no greater than 1000 nanometers. The electric field induced transport is faster for any significant potentials. Based on this qualitative inspection, it is possible to deduct that the ionic current will last only a very short time and an equilibrium is established. This corresponds to a charging of a capacitor. After charging, no ionic current should flow, provided that no electrochemical reactions are happening on the electrode surfaces.

After the electrodes are compressed into a close proximity, the volume between the electrodes is so small that electrochemical reactions consume the electroactive compound very fast. Accordingly, the measurement must also be fast. While this might first seem to be a drawback, it is really a merit. The behavior of the ions depends on the reversibility of the oxidation or reduction much more than in a large traditional electrochemical cell. For a reversible redox reaction the reduced species can diffuse from the cathode to the anode very fast and be reoxidized and then diffuse to the cathode and be reduced again. For an ideally reversible redox reaction the cycle can be repeated without any limit. This leads to a greatly amplified signal. For an irreversible reaction, a gradual increase of an electric potential will deplete the compounds having lowest oxidation or reduction potentials. When the potential increases they do not interfere with the signal obtained form the compounds having higher oxidation or reduction potentials. This is in contrast with bulk electrochemical methods, in which compounds having lower potential continue to give signal during the potential sweep even if the reaction is irreversible.

Figure 17:
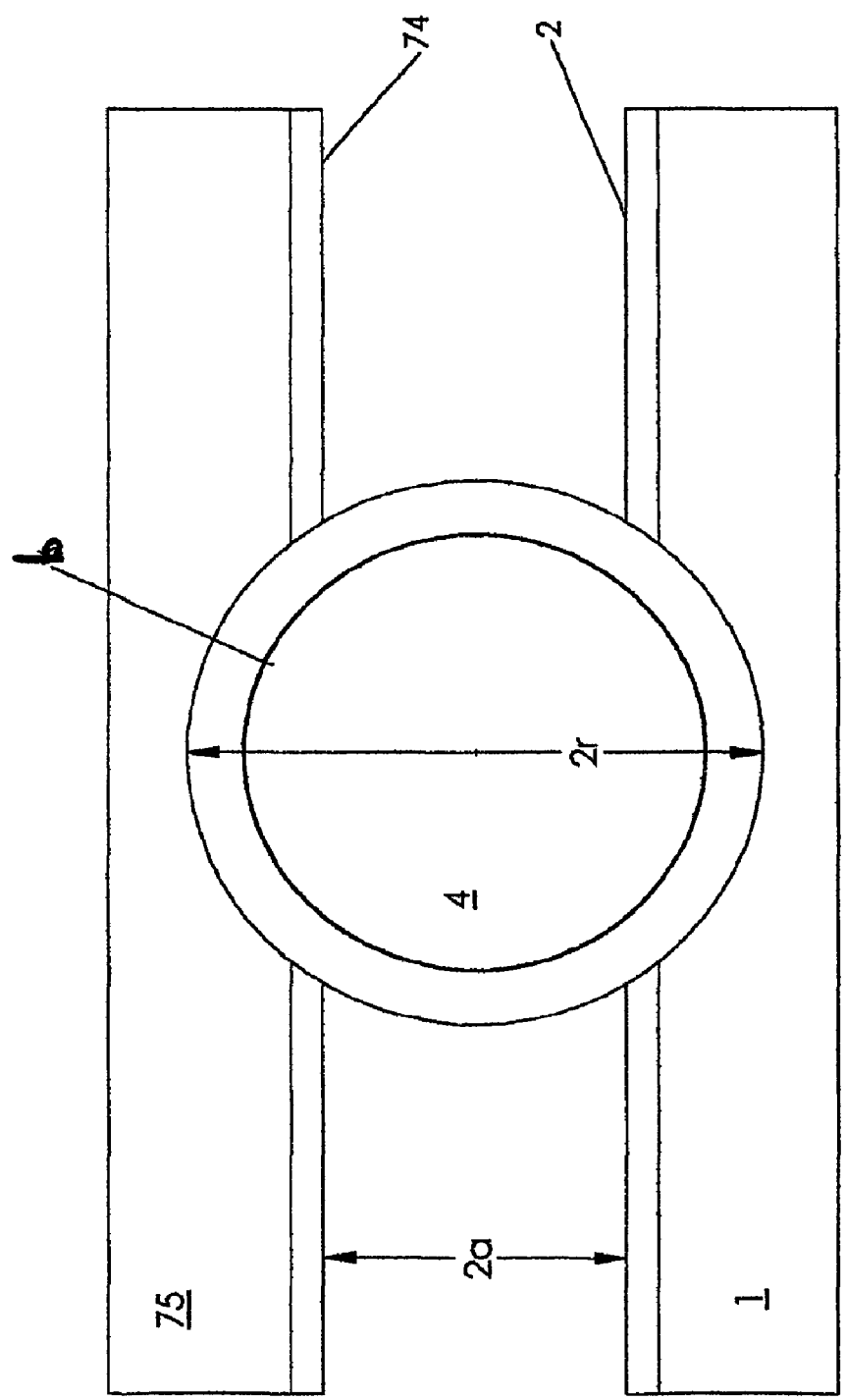
FIG. 17 is a schematic illustration of a gold particle coated with a resistive material.
Figure 18A:
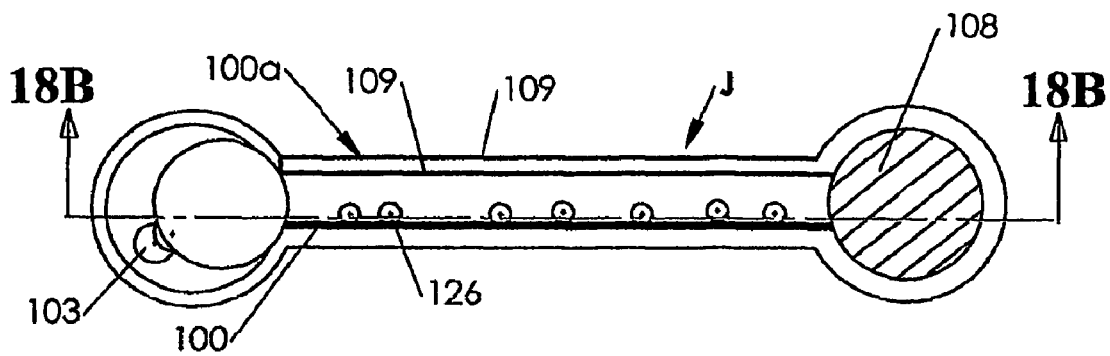
Figure 18B:
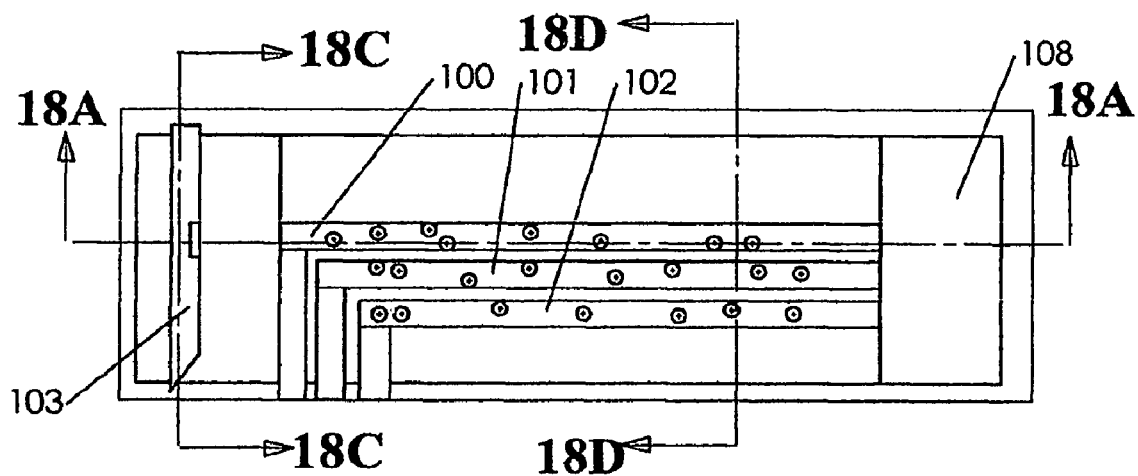
Figure 18C:
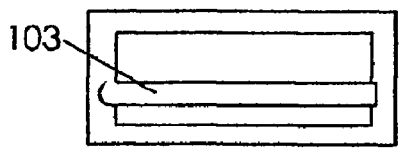
Figure 18D:
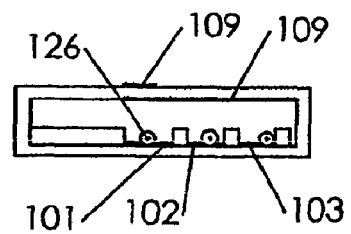

Referring to FIG. 17, the resistance R of a conductive sphere 4 having a radius r is $$R = \frac{\rho}{\pi r}\ln\frac{r+a}{r-a}$$

where a is the distance of the contact area from the center of the sphere. The resistance of a gold sphere that has a radius of 200 nm, and is embedded about 5 nm into a conductive layers on both sides, is about 0.2 Ω. Gold electrodes that have dimensions of 100 nm×1 mm×10 mm have a resistance of 2 Ω. If the particle is coated with a conductive layer of a thickness b, the resistance is $$R = \frac{\rho}{\pi b}\frac{a}{r}$$

The current between electrodes that are connected by N particles is $$I = \frac{\rho}{\pi r}\frac{a}{b}\frac{U}{N}$$

This is a big enough a current to be measured by hand held amperometers. If there is an organic mono- or multilayer between the gold sphere and the electrode, the current must propagate by tunneling. The tunneling current will be only few nanoamperes via one gold particle. Because there are ideally thousands of gold particles in one assay area, the current will be typically micro- or milliamperes.

In some situations, the conductivity of the gold particle is reduced by applying as resistive material as a layer b over the surface of the gold particle as depicted in FIG. 17.

Immunoassays

Antibody-antigen interaction can be used in many different ways either to bind or prevent the binding of electrically readable particles onto a surface of an electrode. In a traditional sandwich type assay one member of a matching antibody pair is bound on to electrically readable particles and the other on to an electrode. The corresponding antigen will form a bridge between two antibodies and bind the electrically readable particle on to the surface of the electrode as is depicted in FIGS. 1A and 3B. This is a preferred approach when an antigen is a large enough molecule to have at least two spatially separated epitopes. Most proteins can be assayed by sandwich assay. A cleavable spacer provides another way to perform a sandwich assay (Virtanen, 1996). The number of the bound electrically readable particles is directly proportional to the concentration of the antigen. For smaller molecules, such as steroids and several drugs, the competitive assay is the method of choice (FIGS. 3A and 3B). The antibody is attached, for example, on to the electrically readable particle, and the antigen or an analog of the antigen is attached onto the electrode. The antigens in the sample saturate the antibody molecules on the electrically readable particles in a concentration dependent manner. The competitive method is not equally sensitive as the sandwich assay, because zero and very small concentrations of the antigen gives maximum or near maximum binding. Small changes are very difficult to differentiate from the normal experimental error.

Currently the preferred electrode material is gold. The gold surface can be first coated with streptavidin, which will adsorb spontaneously from an aqueous solution. Biotinylated antibody will bind with steptavidin providing a good coating. Several other ways of attaching of antibodies onto the gold surface are well known in the art. These include forming a monolayer of polylysine or copolymer of lysine and cysteine on to the gold surface, and attaching periodate oxidized antibody in the presence of sodiumcyanoborohydride on to this monolayer. The simples way is to reduce the antibody with dithiotreitol or with some other reductant and let the reduced antibody to chemisorb directly on to the gold surface. This is currently the preferred method, because the insulating organic layer is very thin, having a thickness of only half of an antibody molecule. The preferred electrically readable particles of gold spheres can be coated with antibodies using exactly the same methods as are used to coat the gold electrode. A wide variety of immunoassays can be performed with the present method. Nonlimiting examples include HCG (pregnancy test) and prostate specific antigen (PSA) detection, insulin, proinsulin, glucagon, glycated hemoglobin, growth hormone, fetoprotein, TSH, C-reactive protein, CK-MB, myoglobin, troponin, interferons, interleukins, ferritin, tumor negrosis factor, trypsin, plasminogen, cardiolipin, cortisol, aldosterone, estradiol, digoxin, benzodiazepine, vancomycin, amphetamine, cocaine, morphine, tetrehydrocannabinol, phenobarbital, secobarbital, parathione, adenovirus, chlamydia, cytomegalovirus, hepatitis viruses, HIV, influenza, and parainfluenza.

Immunoassays and panels are discussed in the following U.S. Pat. Nos. 5,744,358; 5,075,220; 5,030,561; 4,497,900; 4,497,899; and in Kohler et al., "Antigen Detection to Diagnose Bacterial Infections", Boca Raton, Fla., CRC Press, Inc. 1986, pp. 138-144.

DNA Testing

Figure 2B:
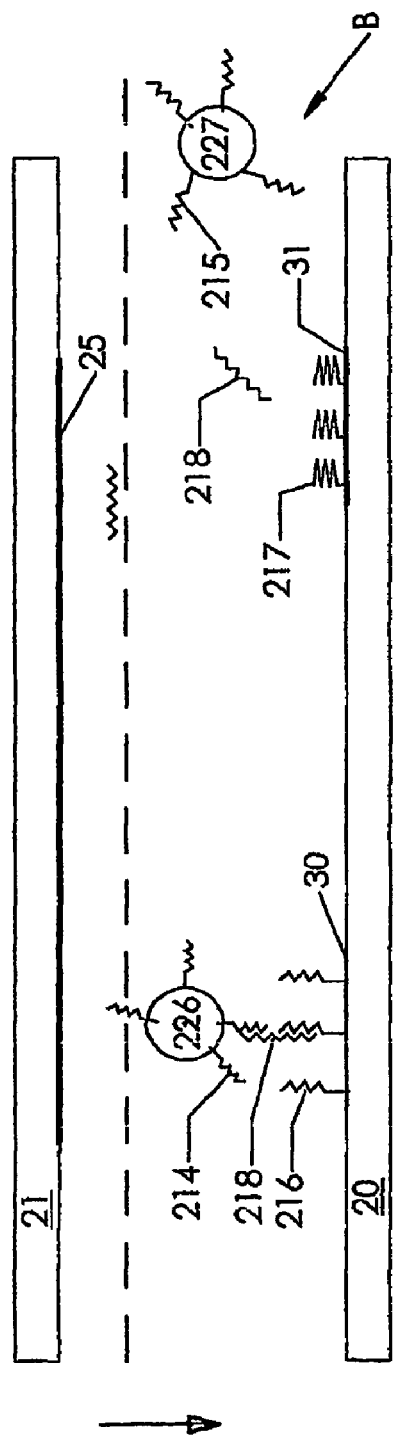
Figure 2C:
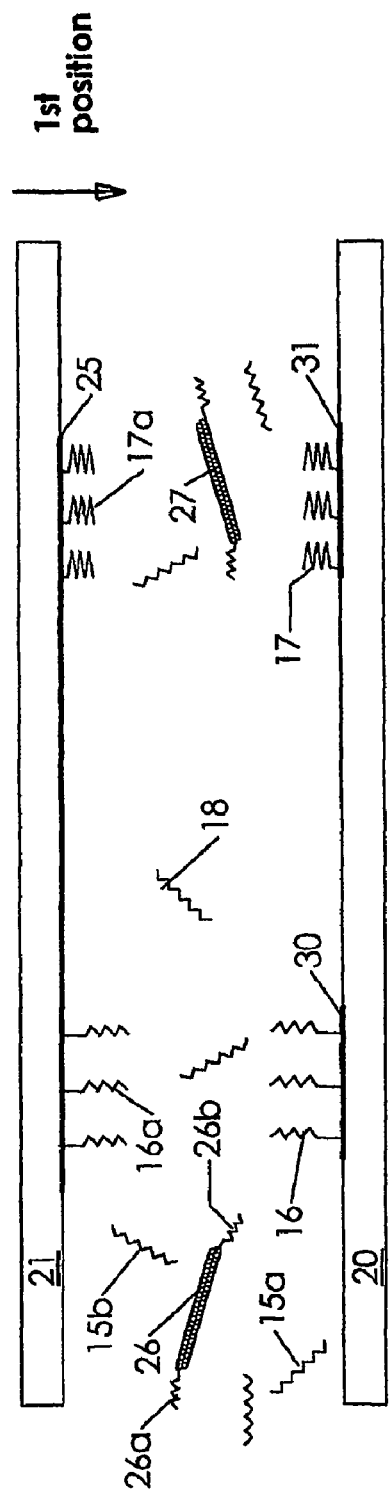
Figure 2D:
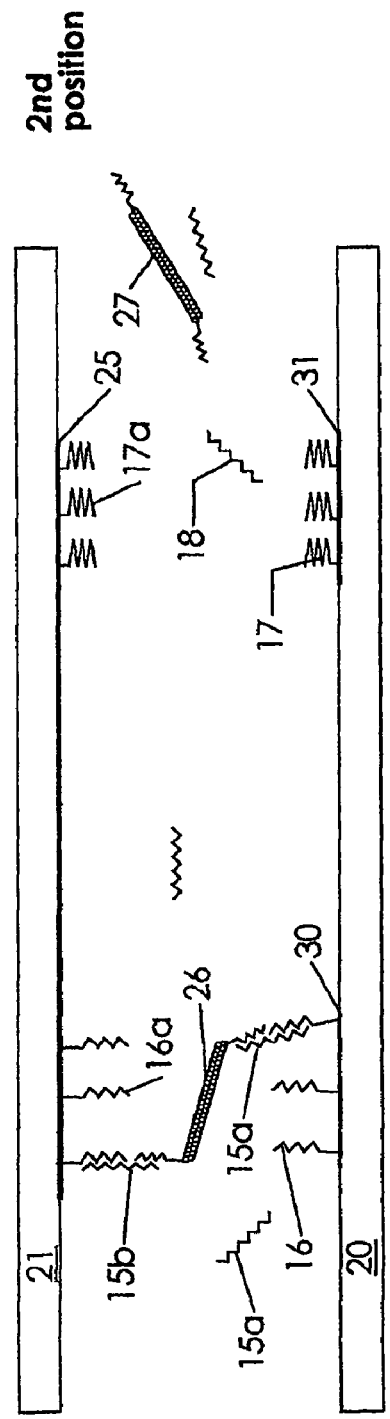

DNA tests are analogous to sandwich immunoassays as is depicted in FIGS. 2A and 2B. The present invention allows testing of tens or even hundreds of thousands of sequences simultaneously. The main large-scale application of oligonucleotide arrays is comparative expression analysis. Gene expression patterns in healthy as well as in diseased tissues and cells will greatly increase the understanding of the function of living organisms. The effect of drugs can be understood in much more detail than presently. Another application for the oligonucleotide arrays is the finding of single nucleotide polymorphisms (SNPs). It is estimated that in the human genome one out of a thousand nucleotides is polymorphic. These SNPs are the main reason for human diversity. Once the SNPs have been characterized and correlated with certain disease states, SNPs can be used to predict an individuals tendency for many diseases including various cancers (Cole et al. (1999) The genetics of cancer-3D model, *Nature Genetics Supplement* 21: 38-41), heart disease (Lusis (2000) Atherosclerosis, *Nature* 407: 233-241), and alzheimers disease. Another example of DNA diagnostics is the detection of fetal DNA in maternal plasma (Lo (2000) Clinical Chemistry 46:1903-1906). These DNA and RNA studies are not limited to humans. Plant genomics have enormous economical importance. Knowledge of pathogen genes and gene expression can be used in diagnostics and for the design of new drugs.

In DNA testing the binding agent is usually called a probe and the analyte is usually called a target. Oligonucleotide probes can be synthesized so that they contain aliphatic amino, mercapto, or other groups. They will bind spontaneously on to an electrode surface. Mercapto groups have a drawback that they tend to be oxidized by the positive electrode (anode). The positive charge is sometimes used to attract sample DNA to the close proximity of the electrode. According to the present invention, particles and not the analytes themselves are attracted to the electrode. The charge of the particles can be opposite to the charge of an analyte. Even, when particles are partially covered by negatively charged oligonucleotide probes, which further bind negatively charged targets, the particles can be positively charged or electrically neutral. Thus, it is possible to use a negative charge to attract these particles. In addition to stabilizing the sulfur-gold bond, the negative charge repels the oligonucleotide probes on the surface of the anode. The probes will be nearly perpendicular to the surface and easily accessible (FIGS. 2A and 2B). In the case when positive charge is used, the probes are likely to lay flat on the surface being sterically hindered. The probes have 5 to 10,000 nucleotides, and preferably 10-80 nucleotides. Long probes have generally genomic origin. The target is often a PCR product (amplicons). Other amplification methods are equally possible, including isothermal and ligation amplification. The probes should have preferably about the same length as the amplicons.

Hybridization conditions are well known in the art. Temperature should preferably be 20° C. below the melting temperature of the dublex. The salt concentration has a very large effect on the melting temperature and kinetics of the hybridization. The melting temperature depends also on the guanidine and cytidine contents of the probes and the target. A higher salt concentration in the buffer and higher C/G-content will increase the melting temperature. The electric current will increase the temperature of the electrolyte. The power input is $P=UI$, where U is the potential and I is the current. The increase in the temperature is $\Delta T=UIt/Cm$, where t is the time and C is the thermal capacity of the medium of a mass m. A certain thin layer of the walls must be included into the mass m. The method of the present invention is less sensitive to the external conditions than most currently used methods. This is due to the electric field that can be utilized to increase the rate of the hybridization as well as to test the stringency of the hybridization.

Polymerase and ligase chain reactions as well as isothermal amplification can be performed in the device of this invention. The temperature cycling (not for isothermal) can obtained by electric potential induced heating between the electrodes or by embedding heating elements near the electrochemical cells. The heating is more effective, if instead of a direct current, an alternating current is used.

Oligonucleotide analogs, such as peptidenucleotide acids (PNAs), and thionucleotide acids, offer often increased stability and/or stringency of hybridization. Oligonucleotide probes may be prehybridized with complementary oligonucleotides. The purpose of this kind of array is to study interaction of biomolecules with double helical DNA.

Electrolytes

As discussed above, the detection of electrolytes is one feature of the present invention, because electrolytes are commonly measured electrochemically. Although electrolytes are most of the time measured via the potential change they cause, the present invention offers some advantage over the traditional electrochemical methods. Bringing the electrodes into close proximity will reduce or eliminate the non-specific ionic background current. A steady state ionic distribution is established very fast, generally in the order of seconds or less. The subsequent current will be due to specific binding or permeation of ions.

Solid state electrodes are currently preferred, because they are easier to store than electrodes containing liquids. Ionic specificity is obtained either by superionic films or by ion selective membranes. Advantageously, a reference electrode is used in addition to working and counter electrodes.

Electrolyte detection is discussed in the following references: U.S. Pat. Nos. 5,401,378; 4,758,325; 4,973,394; 5,234,566; and in D. Ammann, "Ion-Selective Microelectrodes: Principles, Design, and Application", Springer-Verlag, New York, 1986, and A. L. Laskar and S Chandra, "Superionic Solids and Solid Electrolytes. Recent Trends", Academic Press, Inc., New York, 1989.

Small Molecule Assays

As discussed above, the present invention allows the detection of several small molecules including, but not limited to glucose, ethanol, cholesterol, lactic acid, and bilirubin. Conventional techniques for binding are discussed by Wieck et al. (1984) Anal. Chim. Acta 158: 137. These small molecules do not in most cases have any specific binding molecule. Instead, each of these compounds has a specific oxidizing or reducing enzyme. Oxidizing enzymes often consume oxygen for oxidation. Oxygen is reduced typically into hydrogen peroxide instead of water. Hydrogen peroxide can be detected electrochemically that is natural detection method for the present invention. Alternatively hydrogen peroxide can enzymatically oxidize many compounds, such as benzidine, tetramethyl benzidine, p-fluorophenol, or p-fluoroaniline to produce fluoride ion, or some other a secondary stable species that can be detected by an ion selective electrode.

Cell and Pathogen Detection

Cells and pathogens can be detected either by assaying certain surface markers, or their DNA. The methods already described for immunoassays and DNA testing are applicable. The conductive particles can also be bound onto the cell membrane, either before or after being bound onto the surface of an electrode. When electrodes are compressed, the conductive particles are forced into a contact with the electrodes: Examples of cells include the human T&NK cells (CD2 and CD7), T helper cells (CD4), T cells (CD5), suppressor cells (CD8), *E. Coli, Salmonella*, and *Helicobacter pylori*.

Detection Circuits

Typical detection circuits are illustrated in FIGS. 23, 24 and 25.

In the detection circuit X shown in FIG. 23, the electrodes 25 and 30 are on one leg of a conventional Wheatstone bridge circuit 144a having AC current applied across this circuit from the source 140. Resistors 144, 145, and 146 are in the other legs of this circuit 144a. An oscillator 148 provides a signal that varies depending on the electrical characteristics or properties of inductance, resistance, capacitance and/or phase shift that is detected by a phase shift detection circuit 145a.

In the detection circuit Y shown in FIG. 24, the electrodes 25 and 30 are in a DC circuit where an input voltage Vi is applied across a capacitor 155 in parallel connection with the electrode 25 and 30. A charging pulse is applied to the base of a transistor 148 and this transistor's emitter is connected through the diode 160 to the + input of an operational amplifier 149, with a feed back loop 149a connecting the amplifier's output to the − input. The output of the amplifier 149 is applied across a voltage measuring device Vmeas to ground. The voltage measured by the voltage measuring device Vmeas varies depending on the electrical characteristics or properties of resistance and/or capacitance across the electrodes 25 and 30.

The detection circuit Z shown in FIG. 25 is like that shown in FIG. 24, but it is designed to be used with an array of test sites such as depicted in FIG. 9. It additionally includes a multiplexer 165 for connecting the test sites 150, 151, and 152, each including the pair of electrodes 25 and 30, the separate circuits including the diodes 160, 161 and 162, respectively, to the + input of the amplifier 149.

Measurement of the Electrical Properties

Electrical power may be provided by a battery (Galvanic cell), solar cell, electromagnetic radiation, magnetic induction, direct contact with external power source, or by any other commonly known means.

Almost any electrical measurement instrument that is able to measure either voltage, current, capacitance, inductance, impedance, or phase shift can be a part of the present invention (A. J. Bard and L. R. Faulkner "Electrochemical Methods: Fundamentals and Applications", Wiley, New York, 1980). The coupling of these instruments to the processing units and to the networks is well known in the art. Examples can be found in several books, including J. J. Barbarello "PC Hardware Projects, Volume 3" (Prompt Publications, Indianapolis, 1998), W. J. Tompkins and J. G. Webster "Interfacing Sensors to the IBM PC" (Prentice Hall PIR, Englewood Cliffs, 1998), S. McDowell and M. D. Seyer "USB Explained" (Prentice Hall, Upper Saddle River, 1999), and J. Axelson "Serial Port Complete" (Lakeview Research, Madison, 1998). Networks include Local-Area-Networks, and Internet. Networks can utilize among others, metal cables, fiberoptics, or be wireless. The ComponentLab described by Barbarello is especially well suited for the measurement of the electrical properties of the electrode intersections. This instrument is totally controlled and powered by a PC. All electrode intersections can be probed sequentially. The unit also contains an A/D converter. Voltage, resistance, and capacitance can be measured for each intersection, and results can be displayed either in a table or graphical format.

The direct detection of the tunneling current is possible, but the charge-and-leak circuit of FIG. 24, called Charge-and-Leak Amplifier, is one option. In the case of a direct contact between the gold particles and electrodes, the current can be inconveniently big, unless resistors are added into series with the gold particles. A Sample-and-Hold Amplifier (J. J. Brophy, Basic Electronics for Scientists, McGraw-Hill Publishing Co, New York, 1990, p. 234) can be modified so that it can be applied to measure electrical properties of each electrode intersection. Input voltage is constant voltage source. A short pulse, for example 50 µs, is given to the base of a transistor 87.

A very low leakage capacitor 85 is charged via a diode 90. In parallel with this capacitor is the electrode intersection that is a leaking capacitor 80, if electrically readable particles are bound between the electrodes. The voltage is measured through a high impedance Op-Amp 89 that contains field-effect transistors. Without the measurement cell the capacitor would retain over 99% of its charge more than 100 hours. The leakage that is due to the cell will reduce the charge and voltage exponentially. This reduction can be sampled at desired intervals or continuously. The time constant of the leakage can be correlated with the number of electrically readable particles.

EXAMPLES

The following are examples of making the electrodes used in this invention.

Example 1

A 4 inch or 6 inch silicon wafer is spin coated with a resist layer. After photolithography 200 nm of silicon is etched away from the exposed areas (Hsiao, Virtanen, and Penner (1993) Appl. Phys. Lett. 63: 1119-1121) to produce trenches. On to these trenches electrodes will be formed by evaporation or sputtering through a mask. Alternatively, electrodes are made by photolithography. The electrode pattern is clearly visible at this point. The wafer is covered by a resist layer. The disc through a mask is exposed to UV-light to form the assay sites. After washing, the assay sites on the electrode array are uncovered gold surrounded by a resist layer. In order to remove any residue, the whole disc is treated with oxygen plasma. Thiolated oligonucleotides and antibodies are printed by ink jet printer, solenoid printer, or by pins (not to be confused with the electrical pins that provide the contact to external instruments). If assay sites are large enough, a pipetting machine will be used to dispense the oligonucleotide probes. In this example fifteen different recognition molecules are dispensed.

Example 2

An electrode array can be conveniently fabricated starting from a commercially available unprocessed CD-master that is a glass plate coated with photoresist. The thickness of the photoresist is about 200 nm that is ideal for most implementations of the present invention. The CD-master is irradiated by UV-light through a master. The exposed areas are dissolved away. A metal film, for example a nickel film, is evaporated evenly over the patterned master disc. After electroforming the metal is detached and used like a CD-stamper is used in CD production. Molded parts are coated with a metal layer either by sputtering or evaporation. The currently preferred metal is gold. A mask is used to allow the metal to be deposited only on to electrode areas. Chemicals are dispensed as in Example 1.

Example 3

Into 1 ml of 200 nm gold colloid (Ted Pella, Inc.) is dialyzed against PBS. Simultaneously into 100 µl of 1 µM solution of polyallylamine is added 10 µl of 1 mM SPD in PBS in another dialysis tube. After 8 hour dialysis 10 µl of 1 µM solution of polyallylamine in PBS is added into the dialysis tube containing gold colloid. The dialysis is continued 16 hours, and 10 µl of 1 mM solution of SMMM is added. The dialysis is continued 8 hours. Simultaneously anti-human IgG is reduced with dithiotreitol and dialyzed against PBS buffer under nitrogen atmosphere. 100 µl of the antibody solution is added into the gold colloid dialysis tube, and the dialysis is continued another 8 hours under nitrogen atmosphere. The dialysis buffer is changed twice during each dialysis.

Example 4

Each of the fifteen assay sites of an electrode array (Examples 1 and 2) is coated with 10 nl of reduced antibody solution (Example 3). In this example each assay site is coated with the same antibody. However, in a preferred embodiment different recognition molecules are dispensed to each assay site excluding sites that are reserved for calibration, which have duplicates or even multiple repeats. After 30 min the array is washed with PBS. 5 nl of 1 M trehalose solution containing also 0.5% of tween-20 is dispensed by ink-jet printer on to each assay site and the array is lyophilized to preserve the antibodies. In this specific example a dilution series of human IgG is studied by the electrode array. Three of the assay sites are reserved for controls, and the other 12 are used for duplicate measurements for six samples of the dilution series. The gold particles used in this example have a positive charge even above isoelectric point of the antibodies that are attached on to them. The affinity bonding can be sped by applying a negative potential to the assay sites. Non-specifically bonded particles can be removed by reversing the potential before the electrodes are compressed to a close proximity. The current, voltage, inductance, capacitance, and/or some other electrical property of each electrode intersection is measured.

Scope of the Invention

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

The invention claimed is:

1. A portable, single use instrument for collecting a blood sample from a host subject and testing for the presence or absence of an analyte in the collected blood sample, said instrument including a housing having a size that allows the instrument to be hand held by a user, said housing including an orifice in a portion of the housing providing access to an interior of the housing, a testing chamber within the interior of the housing, said chamber including a detection circuit that provides an indication of the presence or absence of the analyte in a blood sample, within the interior of the housing in advance of the testing chamber a supply of electrically readable particles with an agent attached thereto that binds with the analyte, said electrically readable particles being introduced into a blood sample fed to the testing chamber, said detection circuit including
- a pair of electrodes, said agent attaching to one of the electrodes, and
- at least one of said electrodes being moveable between a first position where the detection circuit has a first state and a second position where the detection circuit has a second state when the analyte is present in the sample and attaches to the agent attached to the one electrode to alter an electrical property of the detection circuit,
- a moveable mounting member within the interior of the housing carrying said pair of electrodes, and
- a needle in advance of the testing chamber mounted to the mounting member so said needle can be extended through the orifice after said housing portion makes contact with a host subject to withdraw a blood sample from the subject and then be retracted within the interior of the housing to feed the blood sample into the testing chamber, a vacuum being created in the testing chamber upon movement of the mounting member so the sample flows through the needle into the testing chamber.

2. The instrument of claim 1 including a receptacle along the passageway in advance of the testing chamber holding the supply of electrically readable particles.

3. The instrument of claim 2 where the receptacle includes a solid member comprising a matrix material holding the particles, said matrix material dissolving in the blood sample as said sample flows past said solid member to release the particles.

4. A portable, single use instrument for collecting a blood sample from a host subject and testing for the presence or absence of an analyte in the collected blood sample, said instrument including
- a housing having a size that allows the instrument to be hand held by a user, said housing including
- a needle,
- a cavity into which a collected blood sample flows,
- an orifice in a portion of the housing providing access to the cavity,
- a detection circuit that provides an indication of the presence or absence of the analyte in a collected blood sample flowing into the cavity,
- a moveable mounting member so that upon movement of the mounting member a vacuum is formed within the cavity,
- said needle being mounted on the mounting member so upon the mounting member being moved said needle is moved from a retracted position to a sample collection position with the needle extending through the orifice into the host subject, with a blood sample from the subject flowing through the needle into the cavity due to the vacuum.

5. The instrument of claim 4 where the detection circuit includes a pair of electrodes, one being moveable.

6. A portable, single use instrument for collecting a blood sample from a host subject and testing for the presence or absence of an analyte in the collected blood sample, said instrument including
- a housing having a size that allows the instrument to be hand held by a user, said housing having an orifice therein and containing
- a needle,
- a testing chamber into which a collected blood sample flows,
- a detection circuit in communication with the testing chamber that provides an indication of the presence or absence of the analyte in a collected blood sample flowing into the cavity, said detection circuit including a pair of electrodes, said agent attaching to one of the electrodes, and at least one of said electrodes being moveable between a first position where the detection circuit has a first state and a second position where the detection circuit has a second state when the analyte is present in the sample and attaches to the agent attached to the one electrode to alter an electrical property of the detection circuit,
- a supply of electrically readable particles with an agent attached thereto that binds with the analyte, said electrically readable particles being introduced into a blood sample fed to the testing chamber,
- a moveable mounting member so that upon movement of the mounting member a vacuum is formed within the testing chamber,
- said needle being mounted on the mounting member so upon the mounting member being moved said needle is moved from a retracted position to a sample collection position to draw from a host subject due to the vacuum a blood sample into the testing chamber, and
- one of the electrodes of the pair being mounted to move from the first position to the second position after the blood sample fills the test chamber, said agent binding with any analyte in the blood sample to change the electrical properties of the detection circuit upon the one electrode being moved from the first position to the second position.

7. The instrument of claim 6 including a spring member interactive with the needle that forces the needle through the orifice and into the subject when the needle is in the sample collection position, with a blood sample from the subject flowing through the needle into the testing chamber due to the vacuum.

* * * * *